(12) United States Patent
Tearney et al.

(10) Patent No.: US 11,660,001 B2
(45) Date of Patent: May 30, 2023

(54) METHODS AND SYSTEMS FOR OPTICAL IMAGING OR EPITHELIAL LUMINAL ORGANS BY BEAM SCANNING THEREOF

(71) Applicant: The General Hospital Corporation, Boston, MA (US)

(72) Inventors: Guillermo J. Tearney, Cambridge, MA (US); Milen Shishkov, Watertown, MA (US); Brett Eugene Bouma, Quincy, MA (US); Benjamin J. Vakoc, Cambridge, MA (US); Norman S. Nishioka, Wayland, MA (US)

(73) Assignee: The General Hospital Corporation, Boston, MA (US)

( * ) Notice: Subject to any disclaimer, the term of this patent is extended or adjusted under 35 U.S.C. 154(b) by 200 days.

(21) Appl. No.: 17/130,585

(22) Filed: Dec. 22, 2020

(65) Prior Publication Data
US 2021/0219844 A1    Jul. 22, 2021

Related U.S. Application Data

(63) Continuation of application No. 15/589,029, filed on May 8, 2017, now Pat. No. 10,987,000, which is a (Continued)

(51) Int. Cl.
*A61B 5/00* (2006.01)
*G06T 7/00* (2017.01)

(52) U.S. Cl.
CPC .......... *A61B 5/0084* (2013.01); *A61B 5/0062* (2013.01); *A61B 5/0066* (2013.01); (Continued)

(58) Field of Classification Search
CPC ... A61B 5/0062; A61B 5/0066; A61B 5/0068; A61B 5/0084; A61B 5/6852;
(Continued)

(56) References Cited

U.S. PATENT DOCUMENTS

2005/0251116 A1    11/2005   Steinke et al.

OTHER PUBLICATIONS

Japan Patent Office, Notice of Reasons for Refusal, Application No. 2019-221148, dated May 18, 2021, 8 pages.
(Continued)

*Primary Examiner* — Mark D Remaly
(74) *Attorney, Agent, or Firm* — Quarles & Brady LLP

(57) ABSTRACT

Arrangements, apparatus, systems and systems are provided for obtaining data for at least one portion within at least one luminal or hollow sample. The arrangement, system or apparatus can be (insertable via at least one of a mouth or a nose of a patient. For example, a first optical arrangement can be configured to transceive at least one electromagnetic (e.g., visible) radiation to and from the portion. A second arrangement may be provided at least partially enclosing the first arrangement. Further, a third arrangement can be configured to be actuated so as to position the first arrangement at a predetermined location within the luminal or hollow sample. The first arrangement may be configured to compensate for at least one aberration (e.g., astigmatism) caused by the second arrangement and/or the third arrangement. The second arrangement can include at least one portion which enables a guiding arrangement to be inserted there through. Another arrangement can be provided which is configured to measure a pressure within the at least one portion. The data may include a position and/or an orientation of the first arrangement with respect to the luminal or hollow sample.

14 Claims, 30 Drawing Sheets

Related U.S. Application Data continuation of application No. 14/243,508, filed on Apr. 2, 2014, now Pat. No. 9,646,377, which is a continuation of application No. 11/625,135, filed on Jan. 19, 2007, now Pat. No. 9,087,368.

(60) Provisional application No. 60/761,004, filed on Jan. 19, 2006.

(52) U.S. Cl.
CPC .......... *A61B 5/0068* (2013.01); *A61B 5/6852* (2013.01); *A61B 5/7271* (2013.01); *G06T 7/0012* (2013.01); *G06T 2207/10056* (2013.01); *G06T 2207/10101* (2013.01)

(58) Field of Classification Search
CPC ........ A61B 5/7271; G06T 2207/10056; G06T 2207/10101; G06T 7/0012
See application file for complete search history.

(56) References Cited

OTHER PUBLICATIONS

Japan Patent Office, Trial and Appeal Decision, Appeal No. 2019-16550, Application No. 2017-002748, May 11, 2021, 51 pages.
Japan Patent Office, Notice of Reasons for Rejection, Application No. 2021-190870, dated Jan. 10, 2023, 8 pages.

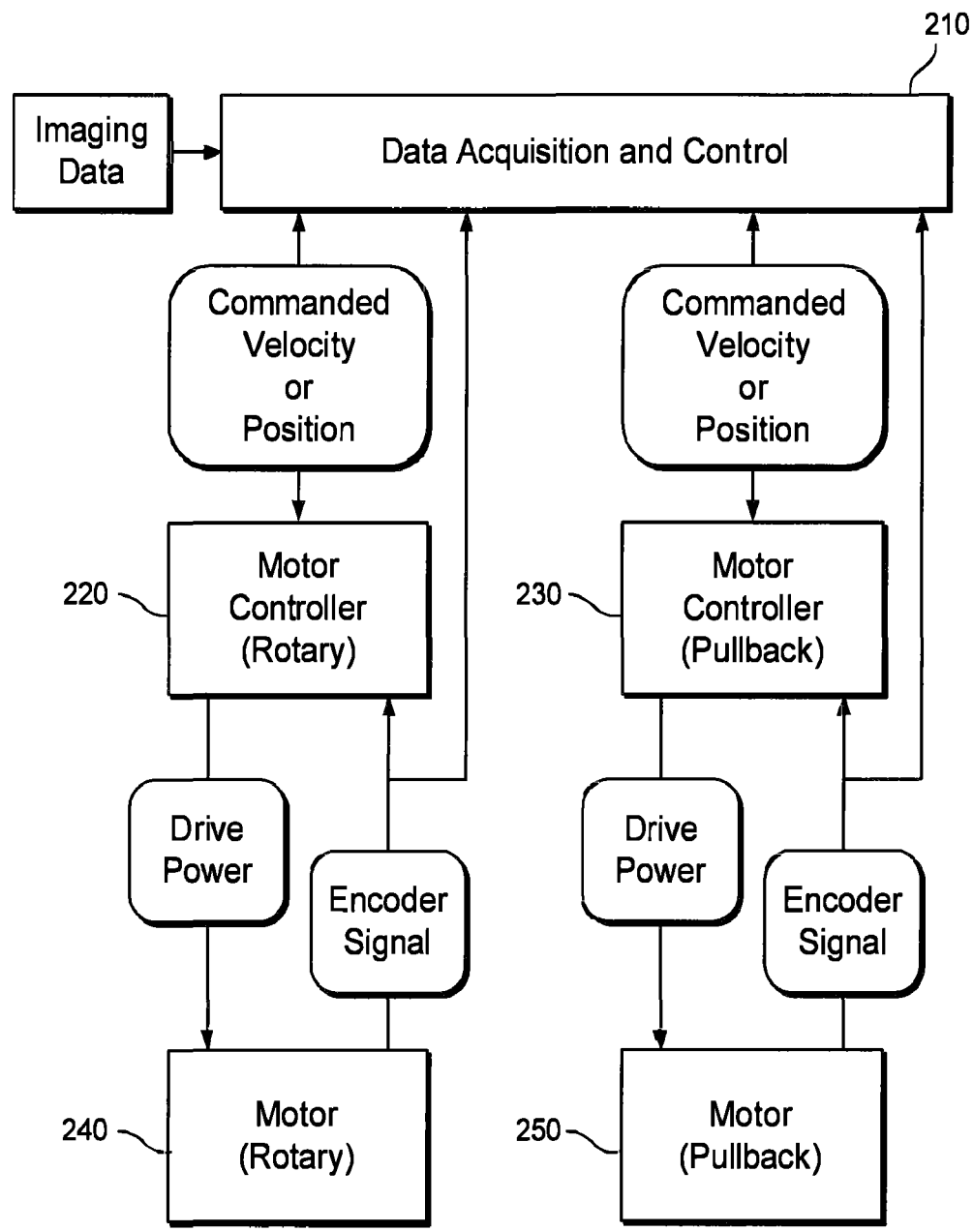
F I G. 5

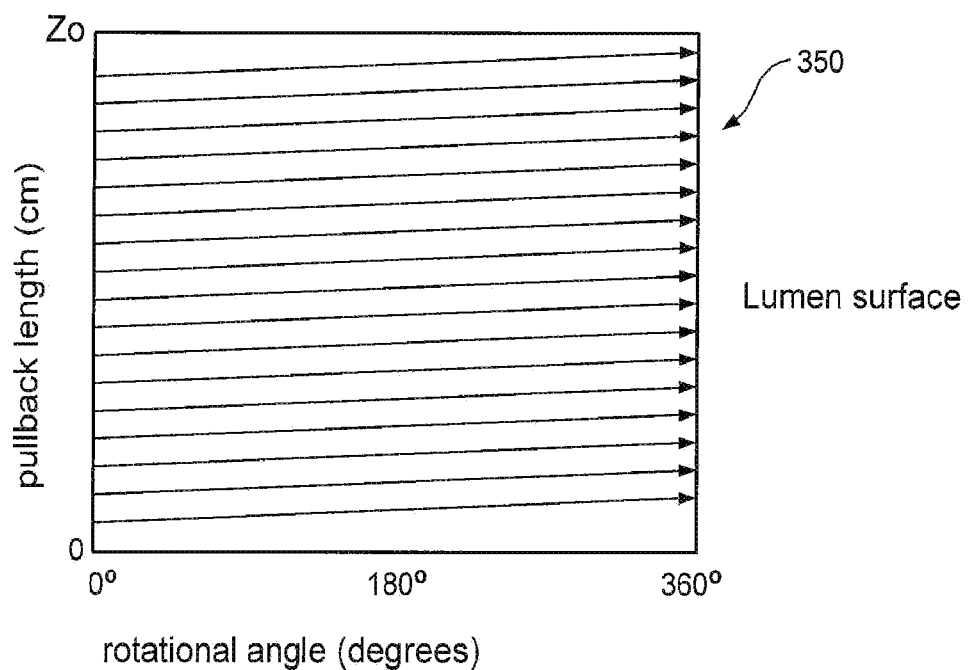
F I G. 7A
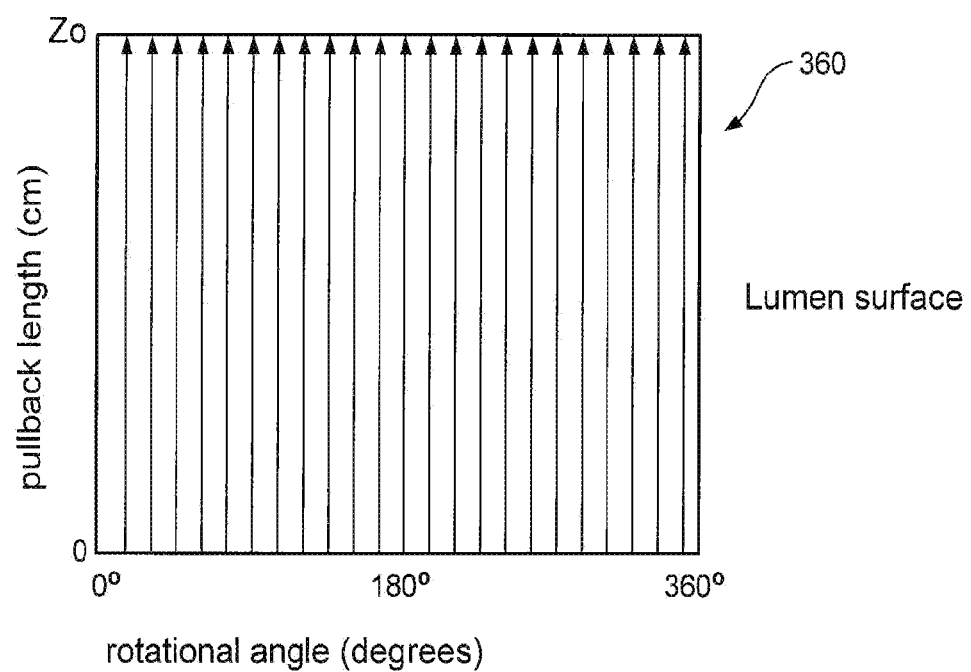
F I G. 7B

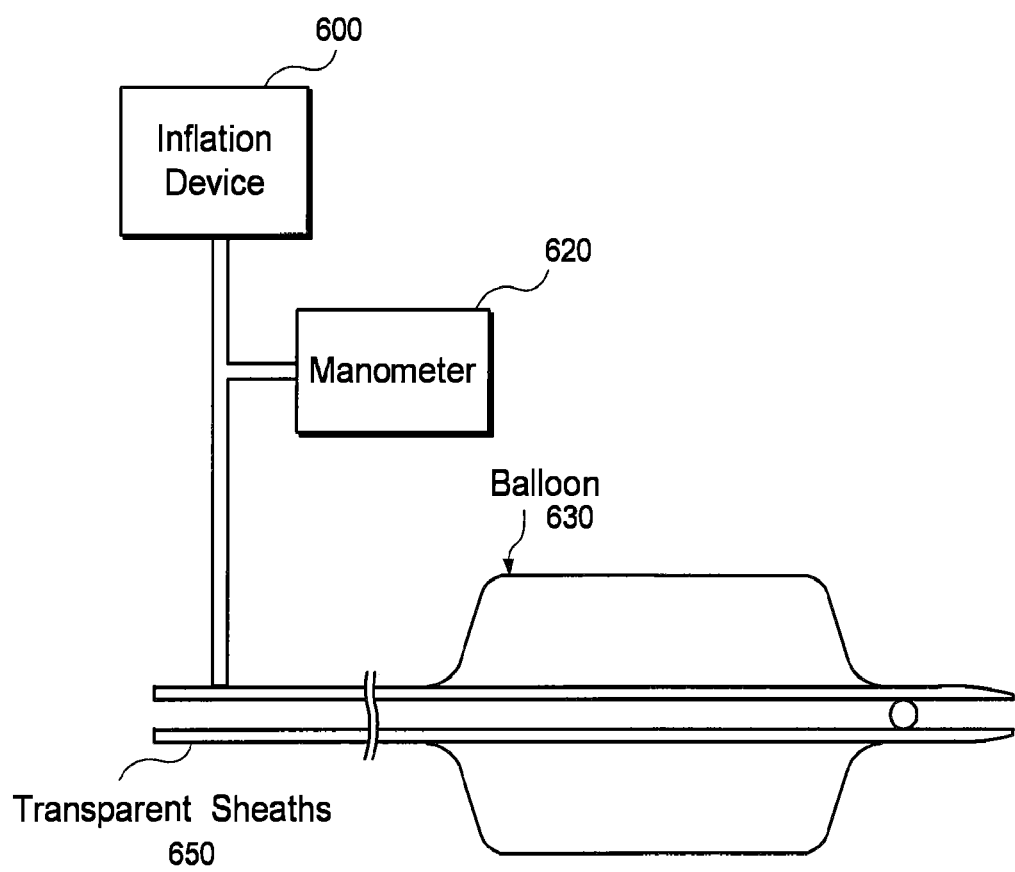
F I G. 10

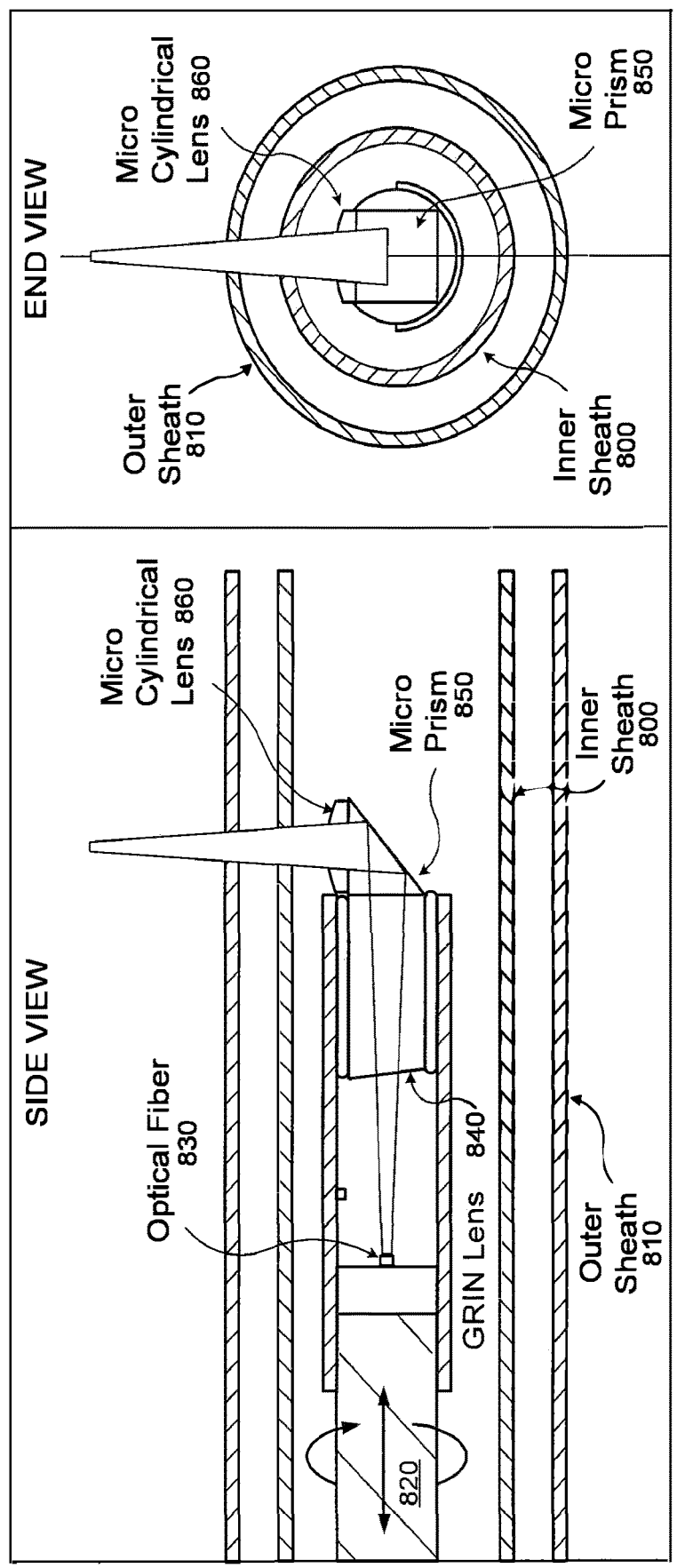
F I G. 12

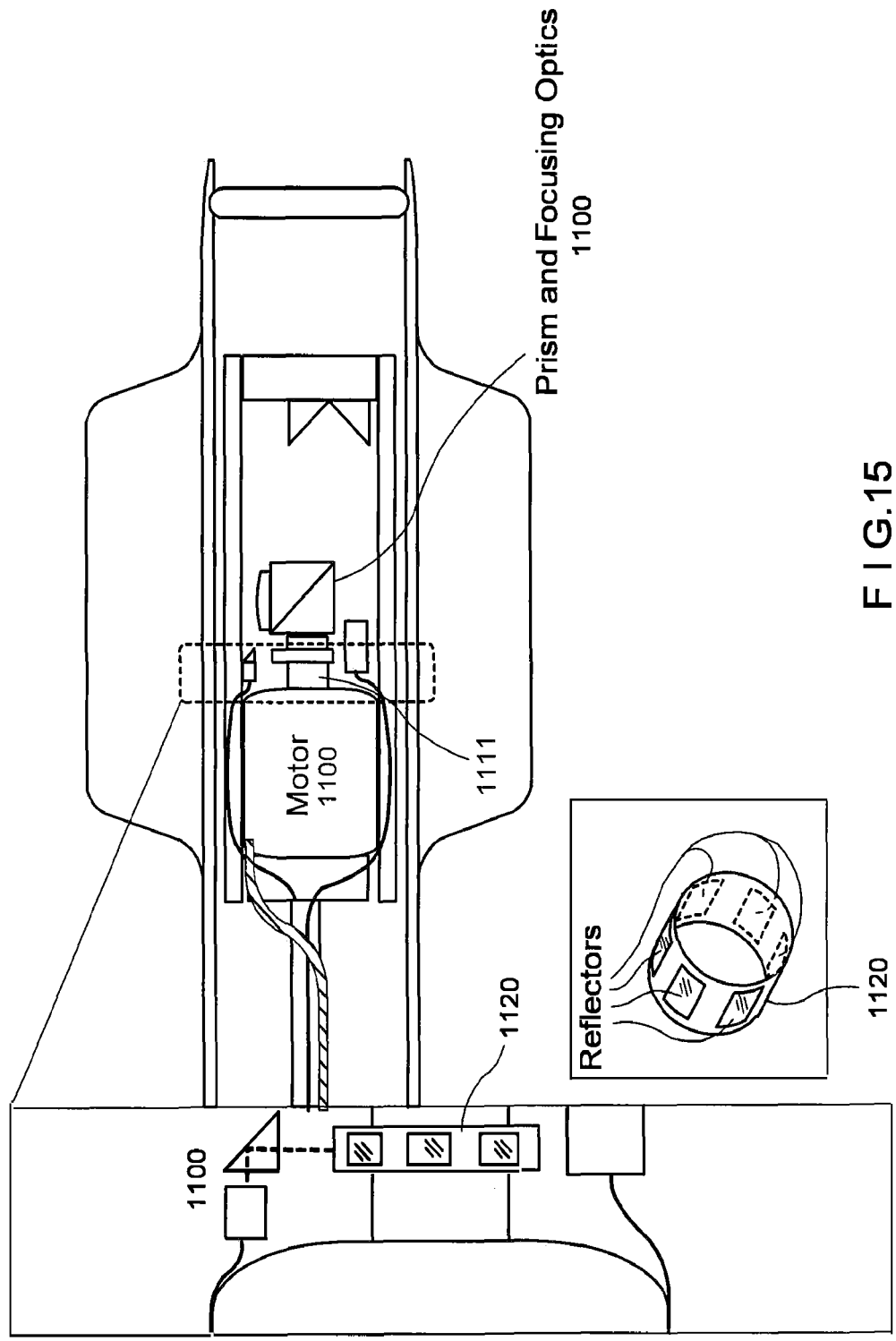
F I G. 15

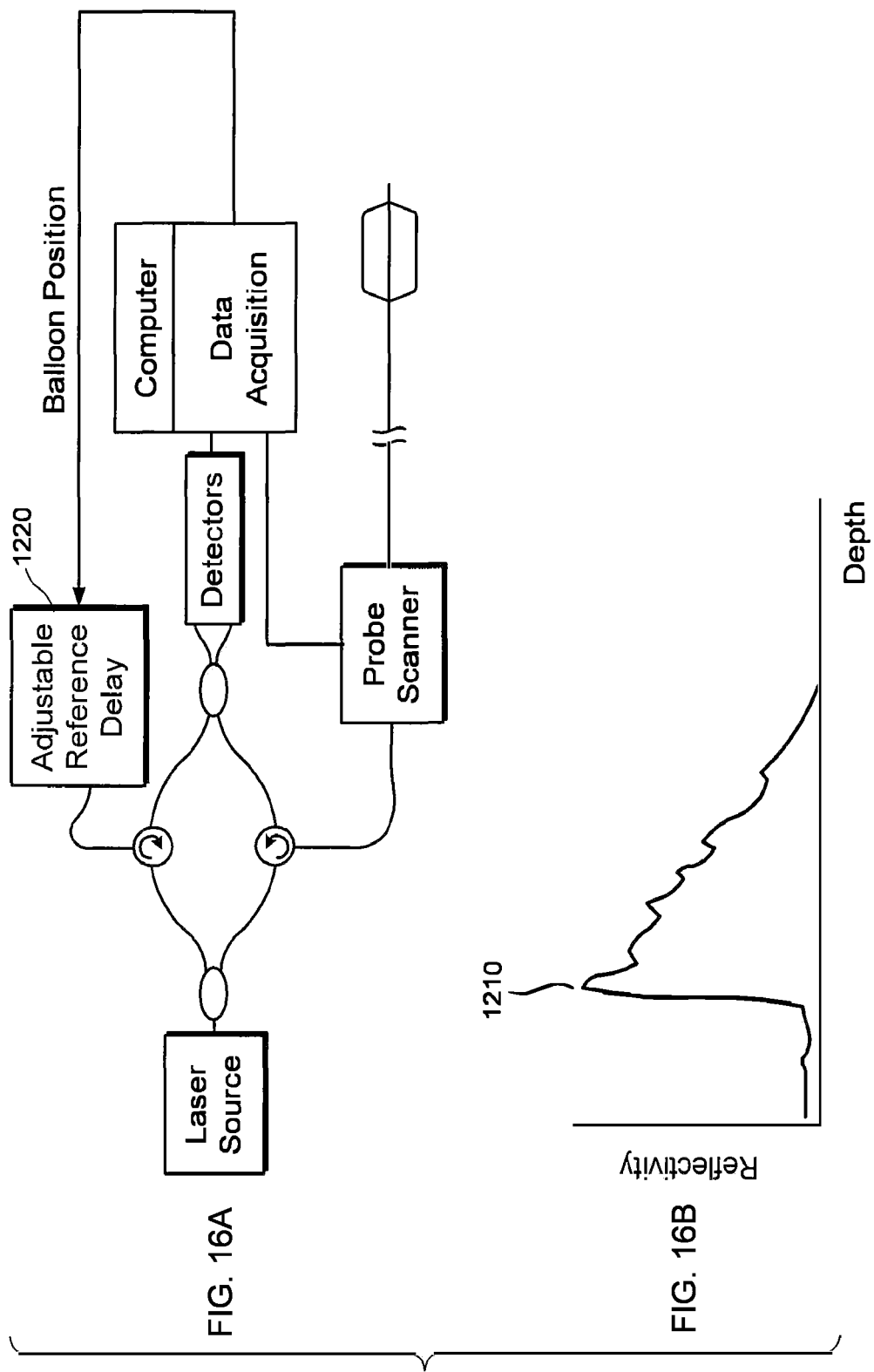

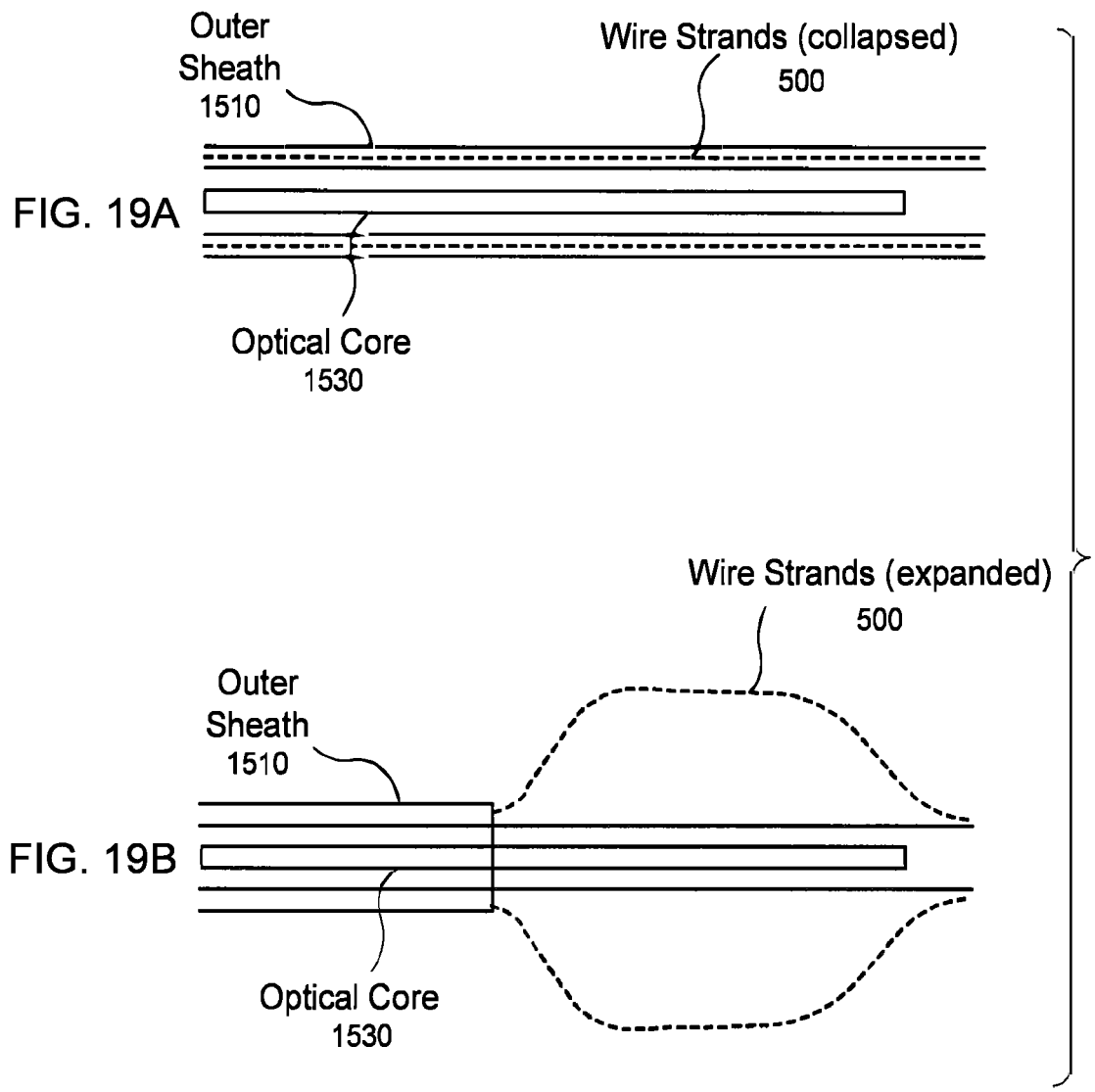

METHODS AND SYSTEMS FOR OPTICAL IMAGING OR EPITHELIAL LUMINAL ORGANS BY BEAM SCANNING THEREOF

CROSS-REFERENCE TO RELATED APPLICATIONS

The present application is a continuation of U.S. application Ser. No. 15/589,029 filed on May 8, 2017 which is a continuation of U.S. application Ser. No. 14/243,508 filed on Apr. 2, 2014, which issued as U.S. Pat. No. 9,646,377 on May 9, 2017, which is a continuation of U.S. application Ser. No. 11/625,135, filed on Jan. 19, 2007, which issued as U.S. Pat. No. 9,087,368 on Jul. 21, 2015. This application is also based upon and claims the benefit of priority from U.S. Provisional Patent Application Ser. No. 60/761,004 filed on Jan. 19, 2006. The entire disclosures of these applications are incorporated herein by reference.

STATEMENT REGARDING FEDERALLY SPONSORED RESEARCH

The invention was made with the U.S. Government support under Contract No. RO1CA103769 awarded by the National Institute of Health. Thus, the U.S. Government has certain rights in the invention.

FIELD OF THE INVENTION

The present invention relates to methods and systems for optical imaging, and more particularly to optically imaging epithelial luminal organs by beam scanning thereof.

BACKGROUND OF THE INVENTION

Screening for diseases is a process whereby a person who is not known to have one or more possible diseases undergoes a test to determine whether or not the person has any such diseases. Screening is often conducted on a large population, and therefore is likely to be inexpensive and minimally-invasive. Surveillance of a patient with a particular disease is a test that is conducted on a person with the disease to determine the severity of such disease, e.g., a degree of dysplasia in a patient with a known pre-cancerous condition. Effective screening and surveillance for the disease (e.g., dysplasia, cancer, etc.) of epithelial luminal organs systems, such as that of the gastrointestinal tract, urinary tract, pancreatobiliary system, gynecologic tract, oropharynx, pulmonary system, etc. utilize a comprehensive evaluation of a substantial portion of the mucosa. Certain beam scanning optical techniques, including time-domain optical coherence tomography ("OCT"), spectral-domain optical coherence tomography ("SD-OCT"), optical frequency domain imaging ("OFDI"), Raman spectroscopy, reflectance spectroscopy, confocal microscopy, light-scattering spectroscopy, etc. techniques have been demonstrated to provide critical information usable for diagnosis of a mucosal disease, including dysplasia and early cancer. However, these techniques are considered point-scanning methods, which are generally capable of obtaining image data only at one location at a time. In order to comprehensively screen large luminal organs, a focused beam can be rapidly scanned across the organ area of interest, e.g., over a large area, while optical measurements are obtained. Catheters, probes, and devices capable of performing this beam scanning function, are therefore generally used for an appropriate application of these and other optical technologies for screening large mucosal areas.

The screening described above should also be inexpensive so as to permit testing of a large population. In order to reduce the cost of screening, it may be preferable to provide a device or systems that is capable of being operated in a stand-alone imaging mode. Such stand-alone imaging can be conducted in unsedated patients, which significantly lowers the cost of the procedure and the complication rate relative to videoendoscopy. For surveillance, the comprehensive imaging procedure can be utilized to direct biopsies to the locations that contain the most severe disease. Since both the imaging and the intervention may occur during the same imaging session, the comprehensive imaging and interpretation of large volumetric data sets should be accomplished in a short amount of time.

Certain challenges exist when using scanned, focused light to comprehensively image luminal organs. Focused spots generally remain in focus for a certain range of distances from the probe to the tissue surface. For certain organ imaging systems, this focal distance (e.g., one metric of which is the Rayleigh range) is significantly smaller than the diameter of the luminal organ. As a result, screening the luminal organ mucosae typically is done by centering the distal/focusing optics of the imaging probe within the organ lumen so that the beam remains in focus throughout the comprehensive scan. Conventional systems employing a centering balloon have been described for OCT imaging of the esophagus. (See G. Tearney, "Improving Screening and Surveillance in Barrett's Patients," NIH Grant No. R01-CA103769; and Boppart et al., "Optical Coherence Tomography: Advanced Technology for the Endoscopic Imaging of Barrett's Esophagus," Endoscopy 2000; 32 (12), pp. 921-930).

Prior clinical studies are known to have acquired images likely only from discrete esophageal locations. The use of such conventional devices used an endoscopic guidance arrangement to identify regions of interest along the esophageal wall, and to direct the imaging probe to these locations. Certain components of the arrangement to provide high-resolution scanning of the focused beam should be considered. For each organ system, a certain catheter/probe types and modes of entry into the patient may be desirable for a less invasive operation. Different centering mechanisms are possible and designs are specific to the anatomy. The beam scanning probe optics should be positioned to the area of interest prior to conducting the imaging without an expensive or complex intervention. The beam focusing mechanism should contain an arrangement for correcting for aberrations caused by the probe sheath/centering mechanisms. In order to obtain accurate large area two- and three-dimensional images of the organ, the position of the beam should be known with precision for each data acquisition point.

Accordingly, there is a need to overcome the deficiencies described herein above.

OBJECTS AND SUMMARY OF THE INVENTION

To address and/or overcome the above-described problems and/or deficiencies, exemplary embodiments of arrangements and processes can be provided that for optical imaging of epithelial luminal organs by beam scanning thereof. These exemplary embodiments of the arrangements and process can utilize a probe and/or disposable portion thereof or of another device which can utilize the following elements and/components for optical imaging of epithelial luminal organs by beam scanning. In particular, these exemplary embodiments can utilize one or more optical waveguides, one or more optics at the distal end to focus the beam, one or more optics at the distal end to redirect the beam, one or more optics at the distal end to correct for optical aberrations, one or more arrangements for scanning beam across the luminal organ surface, a centering mechanism, and a guidewire apparatus.

Thus, in accordance with one exemplary embodiment of the present invention, Arrangements, apparatus, systems and systems are provided for obtaining data for at least one portion within at least one luminal or hollow sample. The arrangement, system or apparatus can be (insertable via at least one of a mouth or a nose of a patient. For example, a first optical arrangement can be configured to transceive at least one electromagnetic (e.g., visible) radiation to and from the portion. A second arrangement may be provided at least partially enclosing the first arrangement. Further, a third arrangement can be configured to be actuated so as to position the first arrangement at a predetermined location within the luminal or hollow sample. The first arrangement may be configured to compensate for at least one aberration (e.g., astigmatism) caused by the second arrangement and/or the third arrangement. The second arrangement can include at least one portion which enables guiding arrangement to be inserted there through.

According to another exemplary embodiment of the present invention, another arrangement can be provided which is configured to measure a pressure within the at least one portion. The data may include a position and/or an orientation of the first arrangement with respect to the luminal or hollow sample. The further arrangement can include a scanning arrangement, the further arrangement detecting the position and the rotation angle by digital counting of encoder signals obtained from the scanning arrangement during at least one scan of the at least one sample. An additional arrangement can be provided which is configured to receive the position and the rotational angle, and generate at least one image associated with the portion using the position and the rotational angle. The additional arrangement may be further configured to correct at least one spatial distortion of the at least one image.

In another exemplary embodiment of the present invention, a processing arrangement may be provided which is capable of being controlled to receive a plurality of images of the sample during at least two axial translations of the first arrangement with respect to the sample. Each of the axial translations may provide at a rotational angle. The data can be interferometric data associated with the sample. The interferometric data may be spectral-domain optical coherence tomography data, time-domain optical coherence tomography data and/or optical frequency domain imaging data.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIG. 5 is a block and flow diagram of exemplary electrical and data connections between components of a control and data-recording mechanism of the exemplary arrangement according to the present invention shown in FIG. 4, including data acquisition and control unit, imaging data, probe scanner motor controllers, and probe scanner motors;

FIG. 7A is an illustration of an exemplary embodiment of a probe scanning method according to the present invention in which the beam is rotated in an accelerated manner, and slowly displaced axially to create a spiral imaging pattern;

FIG. 7B is an illustration of an exemplary embodiment of a probe scanning method in which the beam is scanned axially in an accelerated manner, and then repositioned rotationally and repeated;

FIG. 10 is a schematic diagram of an exemplary embodiment of a balloon arrangement according to the present invention which uses two sheaths and guiding the inflation material (e.g., air or saline) from an inflation channel at the distal portion to the balloon between these sheaths;

FIG. 12 is side and front views of a schematic diagram of an exemplary embodiment of probe optics according to the present invention which includes aberration correction optics (e.g., a micro-cylindrical lens);

FIG. 15 is a schematic side view of an exemplary variant of the balloon catheter shown in FIG. 14 modified to allow a motor position measurement (e.g., encoder) signal to be generated;

FIG. 16A is a block diagram of an exemplary embodiment of a system according to the present invention configured to adjust the reference arm delay in response to the measured balloon position in order to keep the tissue in the system imaging range;

FIG. 16B is a graph of the output of the system of FIG. 16A which is provided as a graph of reflectivity versus depth;

FIG. 19A is a schematic diagram of an exemplary embodiment of a wire cage centering arrangement according to the present invention in a closed mode;

FIG. 19B is a schematic diagram of an exemplary embodiment of the wire cage centering arrangement according to the present invention during the opening starting from a distal portion thereof;

Figure 1:
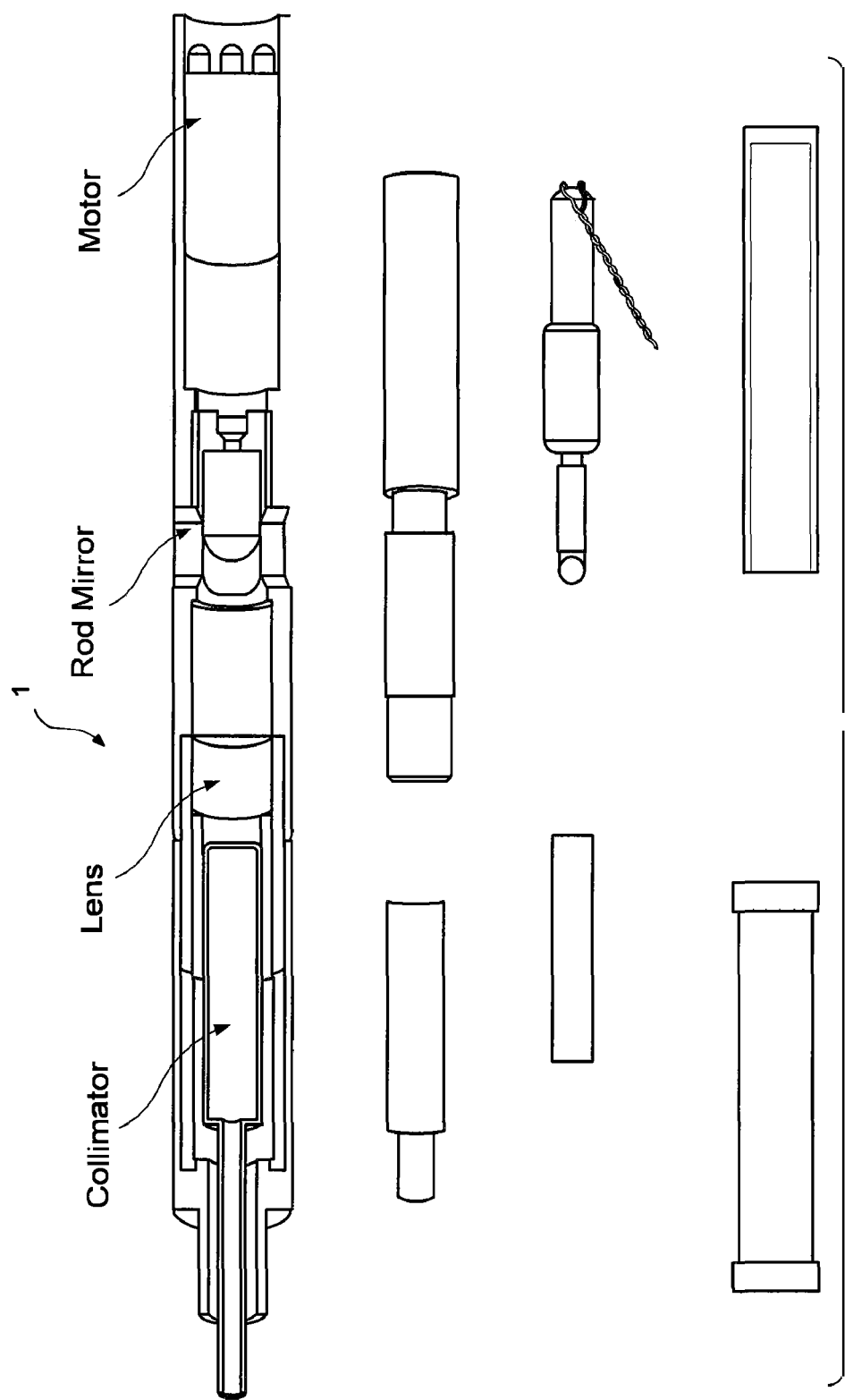
FIG. 1 is a schematic and separated-parts diagram of an exemplary embodiment of a micro-motor catheter according to the present invention which can exclude include a centering mechanism.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

An exemplary embodiment of a prototype esophageal probe 1 in accordance with the present invention was constructed to investigate the feasibility of obtaining images of the entire distal esophagus, the schematic diagram of this exemplary probe is illustrated in FIG. 1. Such exemplary prototype esophageal screening probe 1 was designed to enable acquisition of images of the entire distal esophagus while operating independently of endoscopy, in standalone mode. Imaging of the entire distal esophagus, however, can be a challenging task as the distance between the catheter and the esophageal wall may vary significantly, even under optimal conditions. Since the Rayleigh range over which the images remain in focus is approximately 1 mm (~35 μm spot diameter), the esophageal lumen should be made as circular as possible, and the probe should generally be centered within the esophageal lumen.

Figure 2:
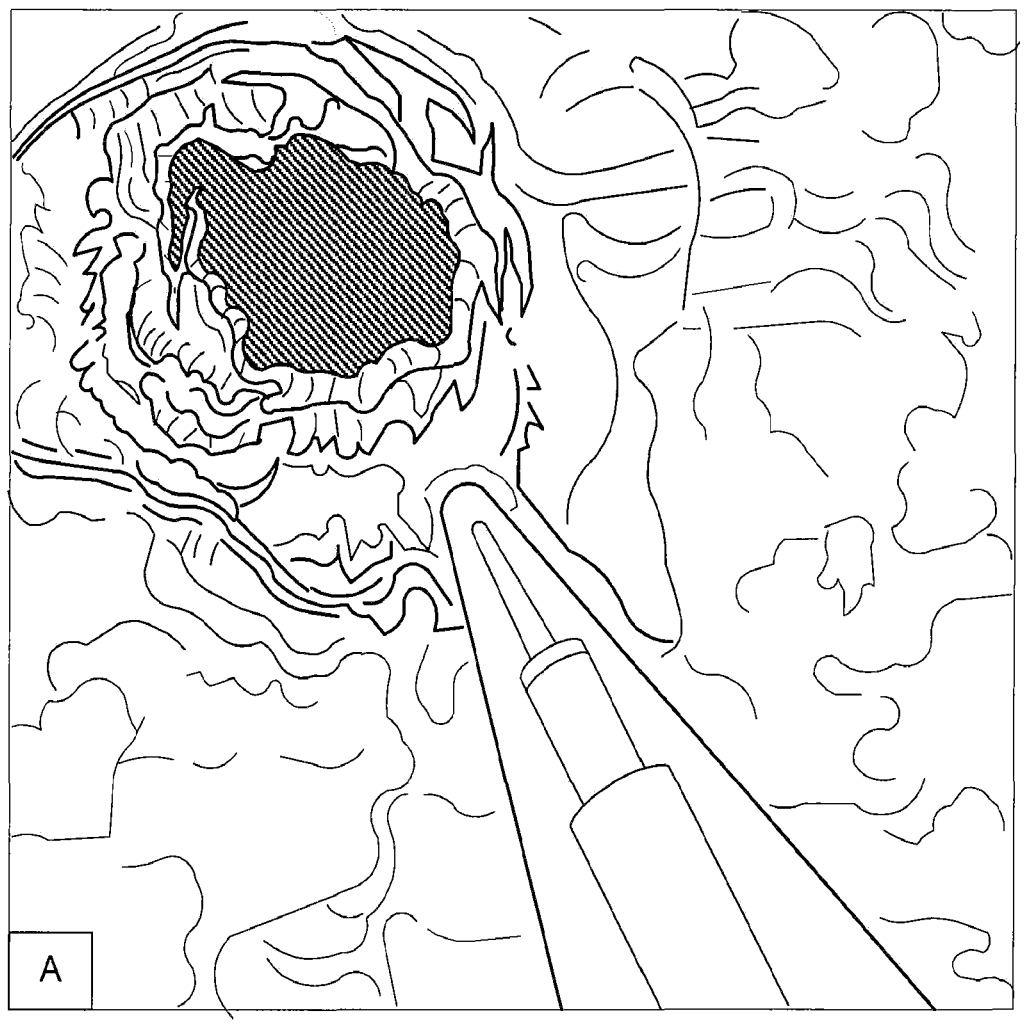
FIG. 2 is a visual image of a linear push-pull catheter that may achieve only a limited large area imaging of a target area of an anatomical structure.

In such exemplary prototype screening probe 1, an esophageal balloon centering catheter (e.g., Eclipse 18x8, Wilson-Cook Medical, Inc.) was used to achieve these tasks. The probe incorporated an inner core containing an optical fiber. The fiber terminated at the distal end of the inner core and the light was focused by a miniature gradient index (GRIN) lens and redirected onto the esophageal surface by a microprism as shown in FIG. 1. The inner core was inserted into the central lumen of the balloon catheter (as also shown in FIG. 1). Using this probe, volumetric images of the distal esophagus were obtained by rapidly rotating the inner core to obtain circumferential cross-sectional images while translating the inner core longitudinally. Volumetric data of a 2 cm diameter porcine esophagus was obtained ex vivo over a longitudinal extent of 3 cm using the prototype probe. Single longitudinal- and cross-sections of the 3D data set demonstrate the capability of this device to obtain high-resolution images throughout the volume. By acquiring images at a rate of 4 frames per second with a pullback velocity of 100 μm per second, the entire volumetric data set was obtained in 5 minutes (see FIG. 2). This exemplary prototype according to the present invention demonstrated that a small-diameter OCT probe can be constructed to obtain high quality and high-resolution images of the entire distal esophagus.

An exemplary embodiment of an apparatus for performing large-area imaging of epithelial luminal organs by beam scanning according to the present invention can be provided. Such exemplary embodiment of the apparatus can include an imaging system, an imaging catheter, and catheter scanner. The imaging system delivers light to the imaging catheter and recovers the light returning from the catheter to generate the image. The imaging catheter directs the light generated by the imaging system to the luminal organ, and focuses this light as a beam directed at the organ luminal surface. The catheter scanner is used to direct the scanning of this beam across a large area of the luminal surface.

Figure 3:
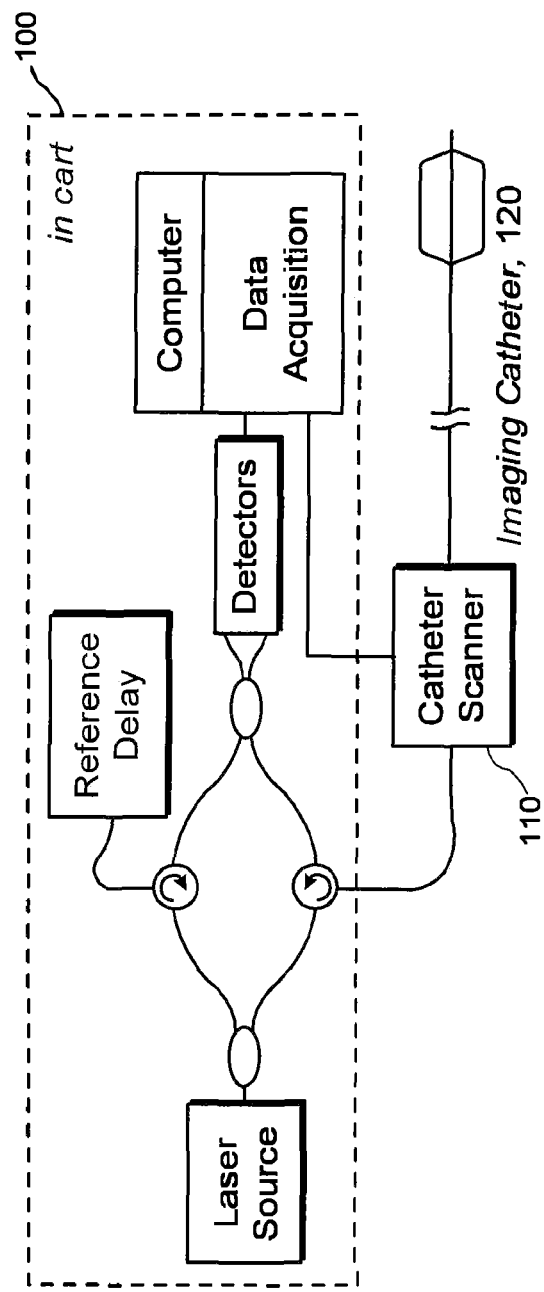
FIG. 3 is a general schematic diagram of an exemplary embodiment of the arrangement according to the present invention, which can include guidewire provision, aberration correction optics, centering mechanism, and rapid beam scanning mechanisms with feedback.

FIG. 3 shows a general schematic diagram of an exemplary embodiment of an arrangement according to the present invention which can include an imaging system. The imaging system can include an optical frequency domain imaging ("OFDI") system 100 (e.g., as described in International Patent Application PCT/US2004/029148, filed Sep. 8, 2004), the catheter scanner is a rotary fiber optic coupler with pullback 110 (e.g., as described in U.S. patent application Ser. No. 11/266,779, filed Nov. 2, 2005), and the imaging catheter is a balloon catheter probe 120. OFDI is a high-speed imaging technology which is similar to optical coherence tomography ("OCT"). The imaging system 100 shown in FIG. 3 can also be a spectral-domain optical coherence tomography ("SD-OCT") system (e.g., as described in U.S. patent application Ser. No. 10/501,276, filed Jul. 9, 2004) or a time-domain optical coherence tomography ("TD-OCT") system. The light from the imaging system 100 can be directed to the catheter scanner 110 which can be a part of a balloon imaging catheter 120.

Figure 4:
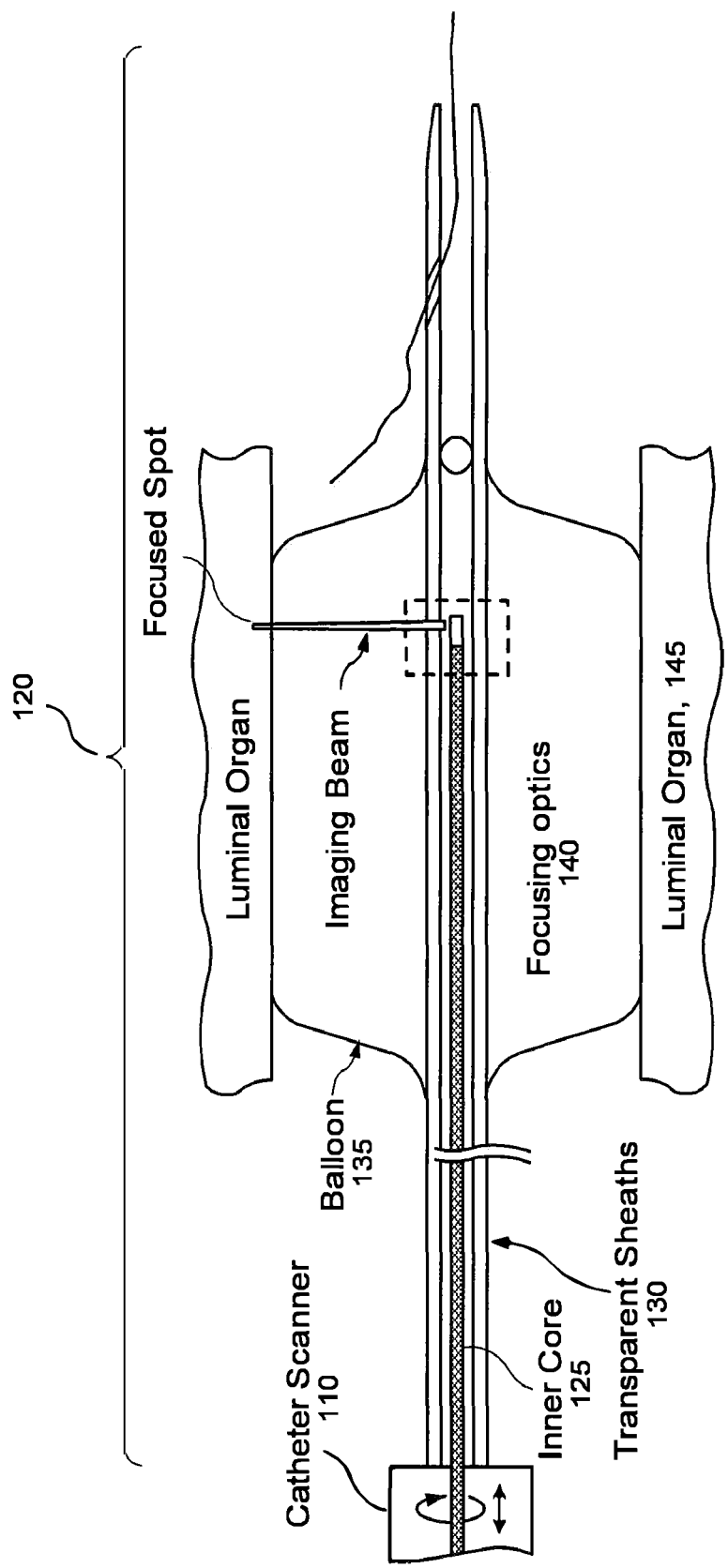
FIG. 4 is a schematic diagram of an exemplary embodiment of an imaging catheter of the arrangement shown in FIG. 3 in use at a target area of an anatomical structure.

FIG. 4 shows a schematic diagram of an exemplary embodiment of the balloon imaging catheter 120 of the arrangement shown in FIG. 3 in use at a target area of an anatomical structure. For example, the catheter scanner 110 may provide light (or other electromagnetic radiation) to an inner core 125 which can be enclosed by optically transparent sheaths 130. At a distal end of the inner core 125, focusing optics 140 can focus and direct the light to the surface of a luminal organ 145 to be imaged. A balloon 135 can be inflated to a center the inner core 125 in the organ 145. The inner core 125 can be configured to rotate and translated axially through the catheter scanner 110, which allows the imaging beam to be scanned over a large area of the organ 145. The inner core 125 can include a fiber optic cable that may guide this light to the distal end of the inner core 125. By recording the signal (e.g., the OFDI signal) as the beam is scanned, a large area of the luminal organ 145 can be imaged.

FIG. 5 a block and flow diagram of exemplary electrical and data connections between components of control and data-recording mechanism the exemplary arrangement according to the present invention shown in FIG. 4. The flow of the data, signals and/or information as shown in FIG. 5 allows the beam position to be recorded simultaneously with the recording of the imaging data to allow for, e.g., a substantially exact spatial registration of the imaging data. As shown in FIG. 5, the imaging data obtained by the OFDI system can be acquired by a data acquisition and control unit 210. The catheter scanner 110 can achieve beam scanning by using a motor 240 provided for rotation and a motor 250 provided for pullback. Each motor 240, 250 can be controlled by a motor controller 220, 230, respectively, in a closed loop operation. The data acquisition and control unit 210 can command the motor controller units 220, 230 to achieve certain motor velocities and/or positions. The encoder signals forwarded from the motors 240, 250 can be configured to be available to both the motor controller units 220, 230 and the data acquisition and control unit 210. As such, each time a depth scan is acquired on the imaging data input, the encoder signals can be recorded for each motor 240, 250, and thus approximately the exact beam position for that depth scan can be recorded.

Figure 6:
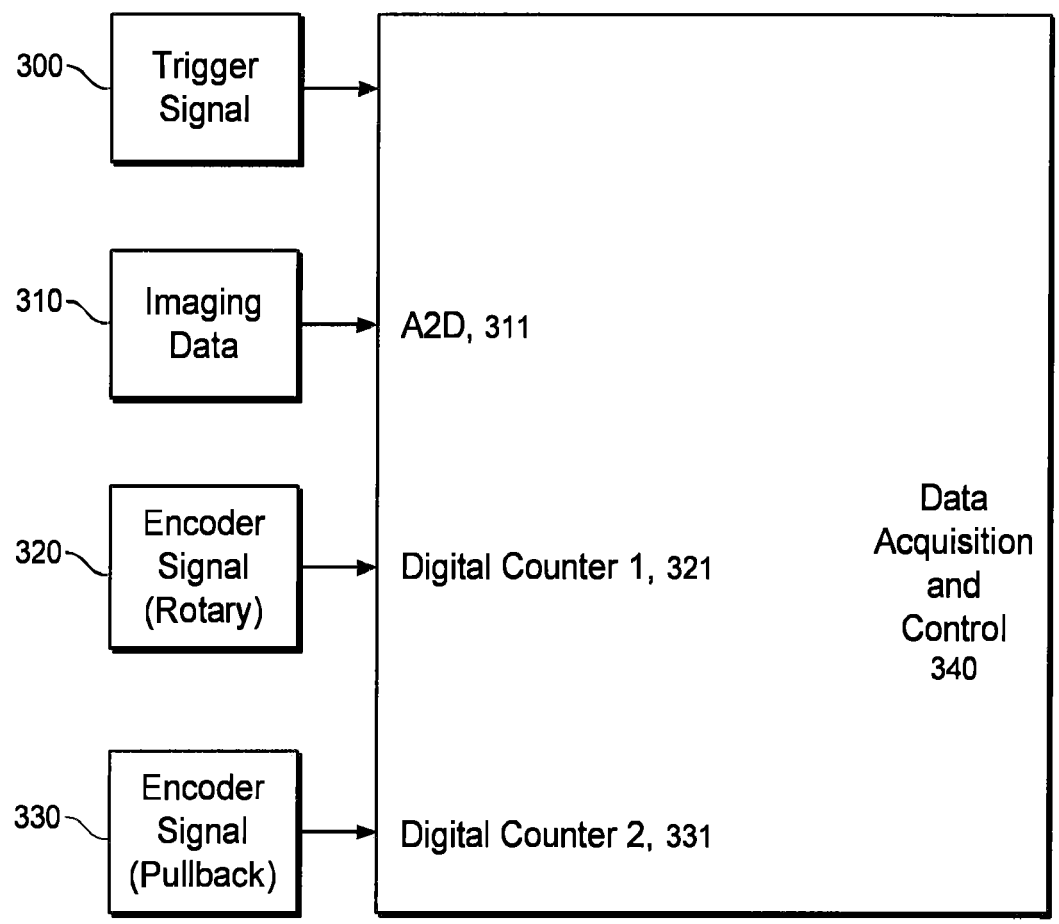
FIG. 6 is a schematic diagram illustrating an exemplary embodiment of a process according to the present invention which enables data to be acquired by the data acquisition unit shown in FIG. 5, and can provide probe position for each measured a-line.

FIG. 6 shows a schematic diagram illustrating an exemplary embodiment of a process according to the present invention which enables data to be acquired by the data acquisition unit 210 shown in FIG. 5, and provide a probe position for each measured a-line. For example, a trigger signal 300 can be used to trigger a single acquisition of a depth scan on an analog to digital (A-D) converter 311, and also to record the value of a digital counter 321 and a digital counter 331 capable of receiving to the rotary motor encoder signal 320 and pullback motor encoder signal 330, respectively. The encoder signals 320, 330 can be TTL pulse trains which may switch at a defined rate per motor revolution. Thus, by counting these switches using digital counters, the current motor positions can be measured. The A-D converter 311 and digital counters 321, 331 can be contained in the data acquisition unit 340.

FIG. 7A shows an illustration of an exemplary embodiment of a probe scanning method 350 according to the present invention in which the beam is rotated in an accelerated manner, and slowly displaced axially to create a spiral imaging pattern. For example, the rotational scanning can occur as a first priority, and the axial (e.g., pullback) scanning can occur as a second priority. This may result in a helical dataset.

FIG. 7B shows an illustration of another exemplary embodiment of the probe scanning method 360 according to the present invention in which the beam is scanned axially in an accelerated manner, and then repositioned rotationally and repeated. In (B), axial (pullback) scanning occurs as a first priority and rotational scanning as the second priority. Because the imaging quality may be best when viewed along the first scan priority, the choice of the scan priority can depend on whether transverse (rotational) images or axial images are needed.

Figure 8A:
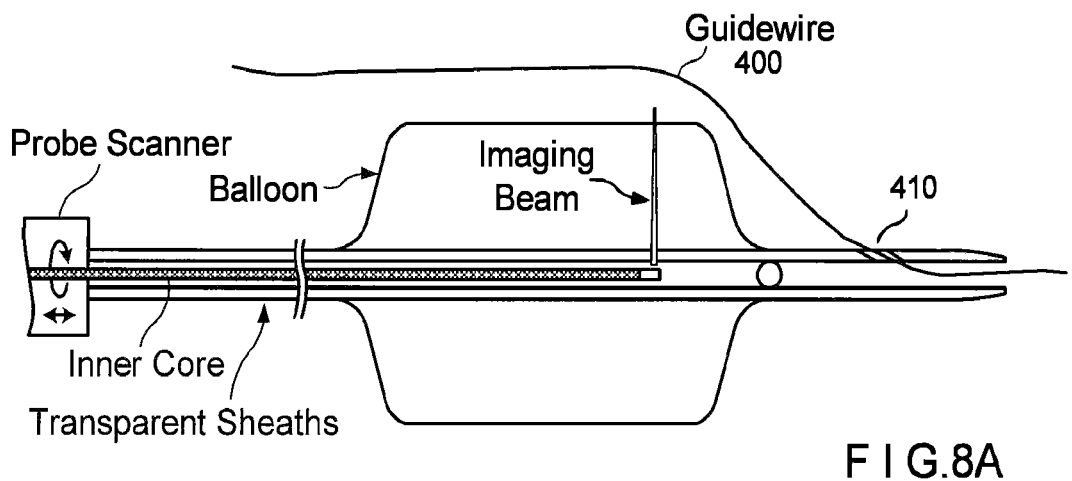
FIG. 8A is a schematic/operational illustration of a first exemplary embodiment of a rapid exchange balloon catheter according to the present invention which includes the guidewire provision located at the tip.
Figure 8B:
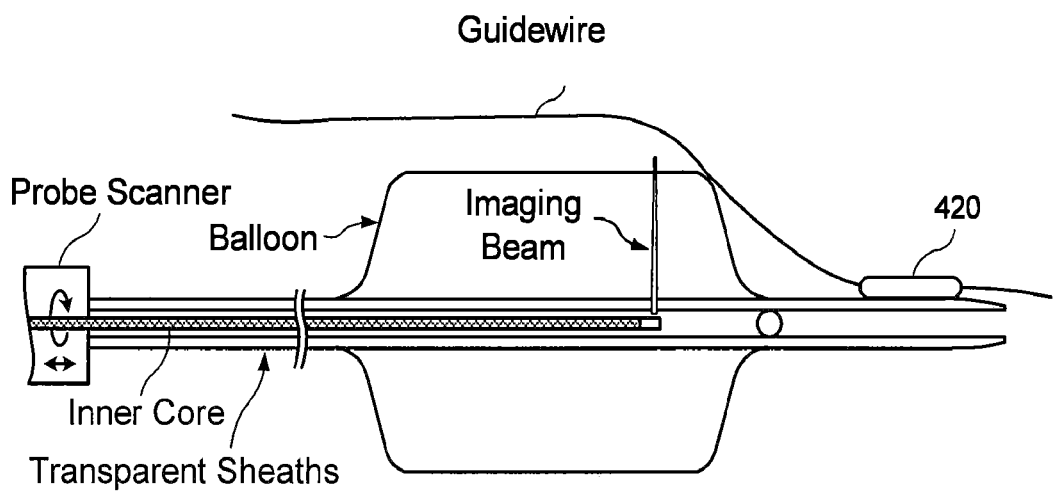
FIG. 8B is a schematic/operational illustration of a second exemplary embodiment of the rapid exchange balloon catheter according to the present invention which includes the guidewire provision located at the tip as a secondary channel.
Figure 8C:
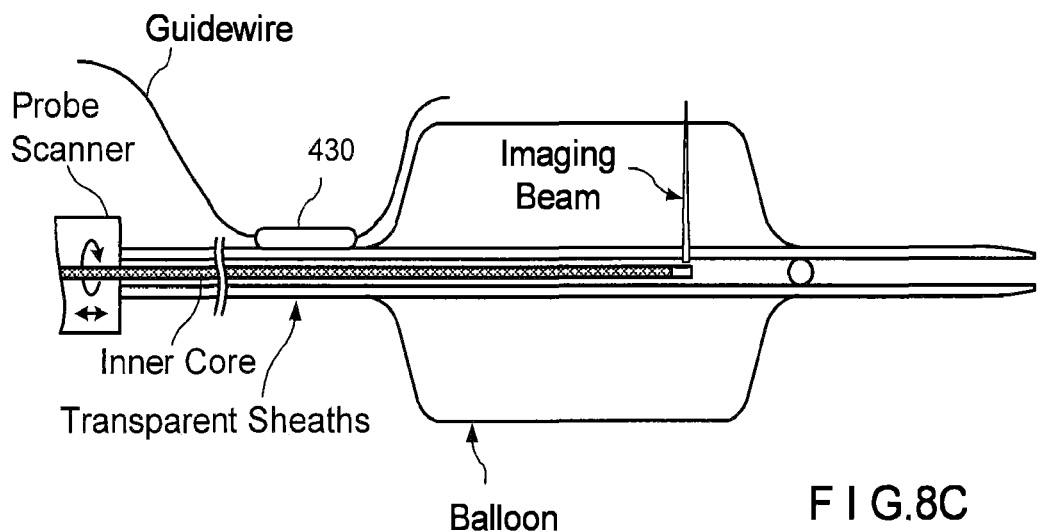
FIG. 8C is a schematic/operational illustration of a third exemplary embodiment of a rapid exchange balloon catheter according to the present invention which includes the guidewire provision located prior to the balloon as a secondary channel.

FIG. 8A is a schematic/operational illustration of a variant of the exemplary embodiment of a rapid exchange balloon catheter 120 as described above with reference to FIG. 3 which includes the guidewire provision located at the tip. In this exemplary embodiment, it is possible to include a rapid-exchange placement thereof over a guidewire. In particular, for the rapid-exchange placement, a guidewire 400 can be first placed in the organ to be imaged, and the catheter may then be threaded along the guidewire 400. This exemplary technique according to the present invention makes the placement of the catheter significantly easier in a number of applications. For example, as shown in FIG. 8A, a guidewire provision can be located by placing a through-hole 410 in the distal end of the sheath of the balloon catheter 120. FIG. 8B shows a schematic/operational illustration another exemplary variant of the rapid exchange balloon catheter 120 according to the present invention which includes a guidewire provision is located by attaching a second tube 420 to the distal end of the balloon catheter 120. FIG. 8C shows a schematic/operational illustration yet another exemplary variant of the rapid exchange balloon catheter 120 according to the present invention, in which a tube 430 is located on the proximal side of the balloon.

Figure 9A:
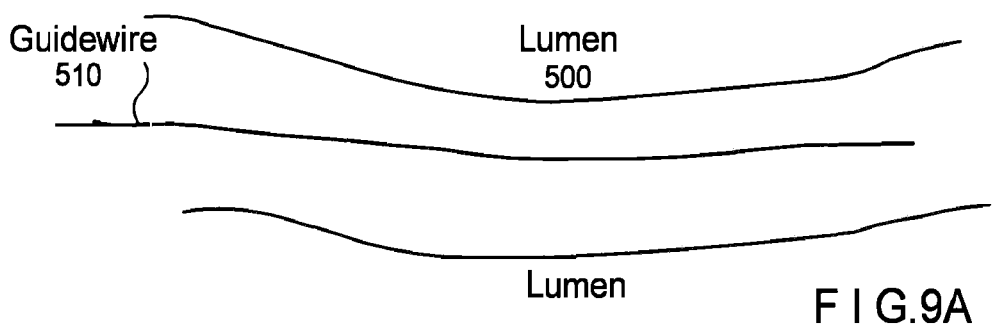
FIG. 9A is an exploded view of the use of an exemplary embodiment of an over-the-wire balloon catheter according to the present invention during the insertion of a guidewire.
Figure 9B:
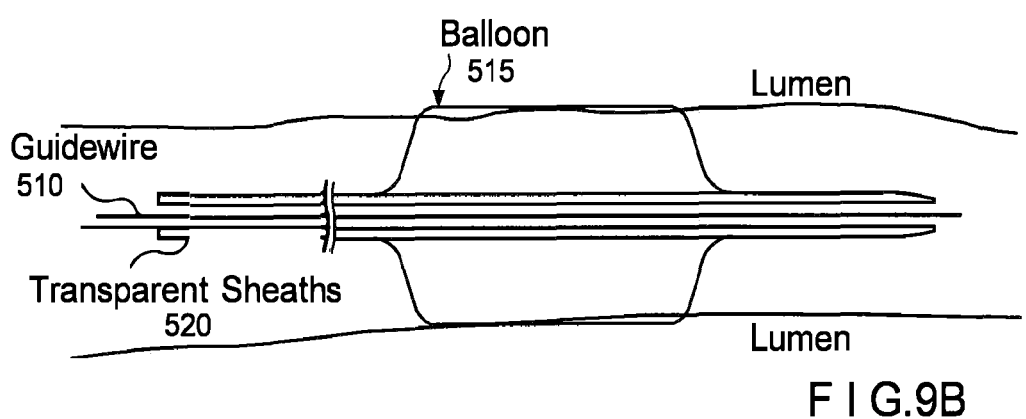
FIG. 9B is an exploded view of the use of the exemplary embodiment of the over-the-wire balloon catheter according to the present invention during the placement of a balloon catheter over the guidewire.
Figure 9C:
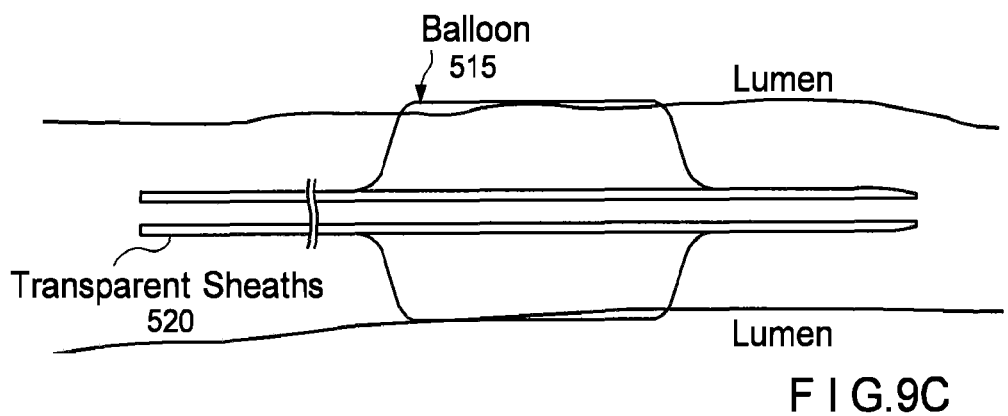
FIG. 9C is an exploded view of the use of the exemplary embodiment of the over-the-wire balloon catheter according to the present invention during the removal of the guidewire.
Figure 9D:
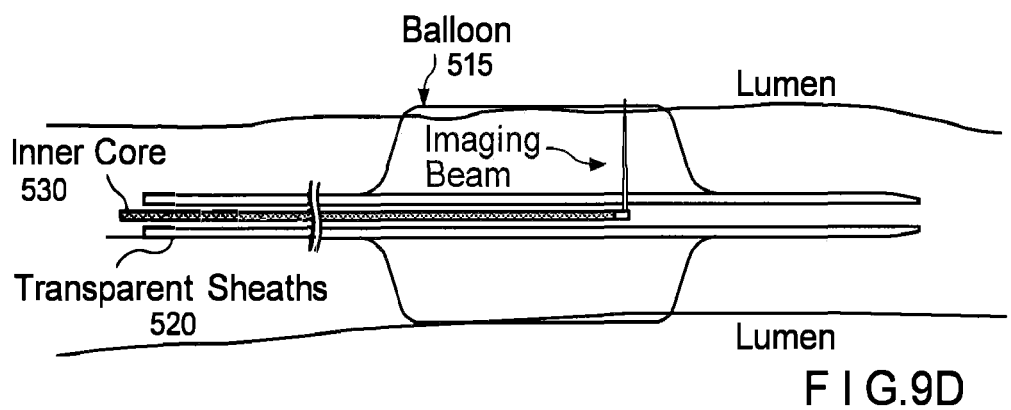
FIG. 9D is an exploded view of the use of the exemplary embodiment of the over-the-wire balloon catheter according to the present invention during the placement of optics in the balloon.

FIGS. 9A-9D are exploded views of the use of an exemplary embodiment of an over-the-wire balloon catheter which uses a guidewire 510 in a central lumen thereof according to the present invention during the insertion of a guidewire. In FIG. 9A, the guidewire 510 is placed in the organ 500. Then, in FIG. 9B, the catheter is threaded over the guidewire 510 such that the guidewire 510 is enclosed in the center lumen 520 of the catheter. The guidewire 510 is then removed in FIG. 9C. Further, in FIG. 9D, inner core optics 530 are threaded down the catheter center lumen 520, and imaging is initiated.

FIG. 10 shows a side view of a schematic diagram of an exemplary embodiment of a balloon catheter which includes a device 600 that can be used to inflate the balloon. For example, the pressure of the balloon 650 may be monitored using a manometer 620. This pressure can be used to optimize the inflation of the balloon 630, as well as assess the placement of the catheter by monitoring the pressure of the organ.

Figure 11:
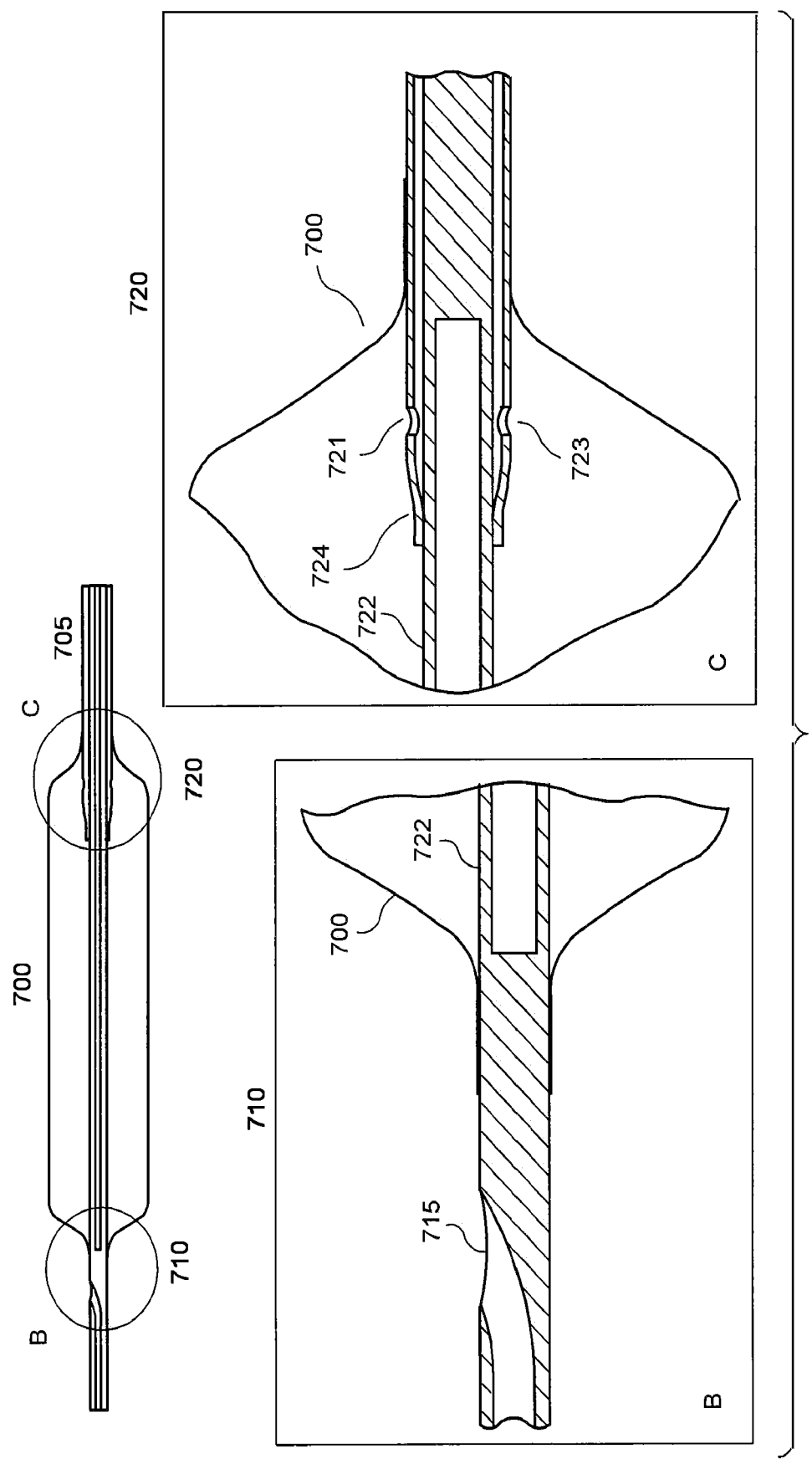
FIG. 11 is a schematic diagram of an exemplary embodiment of a balloon catheter which allows the imaging window to contain a single sheath.

FIG. 11 shows a schematic diagram of an exemplary embodiment of a portion of a balloon catheter which allows the imaging window to contain a single sheath. For example, the balloon 700, its proximal attachment 720 and its distal attachment 710 to a catheter inner sheaths 705 are shown in this figure. In the distal attachment 710 shown in detail in section B, a hole in the sheath 715 can be included to accept a guidewire for use in rapid-exchange catheters (as described above and shown in FIGS. 8A-8C). The balloon 700 can be attached to the inner sheath 722, which extends over the extent of the balloon. The details of the proximal attachment 720 of the balloon 720 are shown in section C. The balloon 720 attaches to an outer sheath 721, which terminates shortly after entering the balloon 720. This outer sheath 721 can be bonded to the inner sheath 722. Two holes 724 and 725 may be provided in the outer sheath 721 such that the balloon can be inflated through the channel created by the inner and outer sheaths 721, 722. One of the exemplary advantages of this exemplary design of the balloon catheter is that there is a single sheath extending along and in the majority of the balloon 720. Because these sheaths may introduce aberrations in the imaging beam and degrade imaging quality, the ability to have one instead of two sheaths in the balloon can improve image quality.

FIG. 12 shows side and front sectional view of focusing optics at the distal end of an inner core of an exemplary embodiment of the catheter according to the present invention. The light or other electromagnetic radiation provided via an optical fiber 830 can be expanded and focused by a GRIN 840 lens. The focal properties of this lens 840 may be selected to place the focal point of the beam near the organ lumen. A micro-prism 850 can reflect the beam by approximately 90 degrees. A small cylindrical lens 860 may be attached to the micro-prism 850 to compensate for the astigmatism of the beam induced by sheaths 800 and 810. Alternately, the micro-prism 850 itself can be polished to have a cylindrical curvature on one side to achieve this astigmatism correction.

Figure 13:
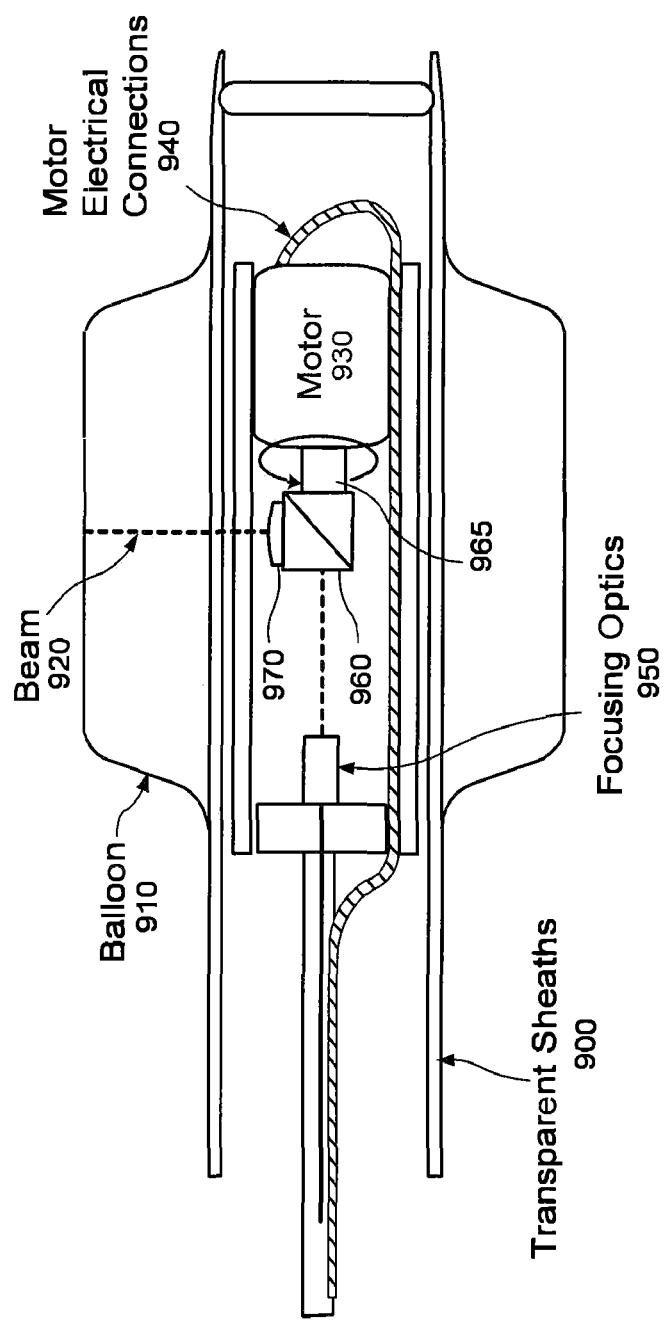
FIG. 13 is a schematic side view of another exemplary embodiment of a balloon catheter according to the present invention which uses a backward facing in-catheter motor to rotate the imaging beam.

FIG. 13 is a schematic diagram of an exemplary implementation and another exemplary embodiment of the arrangement according to the present invention, e.g., beam scanning in the exemplary balloon catheter probe. In particular, the rotational scanning can be achieved by placement of a micro-motor 930 inside the catheter itself. As shown in FIG. 13, the motor 930 can be placed at the distal end of the catheter, and the optical fiber 950 may be directed to a prism 960 mounted on the motor shaft 965. Exemplary electrical connections 940 to the motor 930 can be passed through the imaging path to the motor 930, possibly causing a slight obstruction of the imaging beam. A balloon can be used to center this optical core in the luminal organ. A cylindrical lens or other astigmatism correction optics 970 may be provided on or at the prism to compensate for astigmatic aberrations caused by passage through a transparent sheath 900. Axial scanning can be achieved by translation of the entire optical core, including the focusing optics and the motor 930 within the catheter transparent sheath 900. This translation may be affected by a pullback device at the distal end of the catheter.

Figure 14:
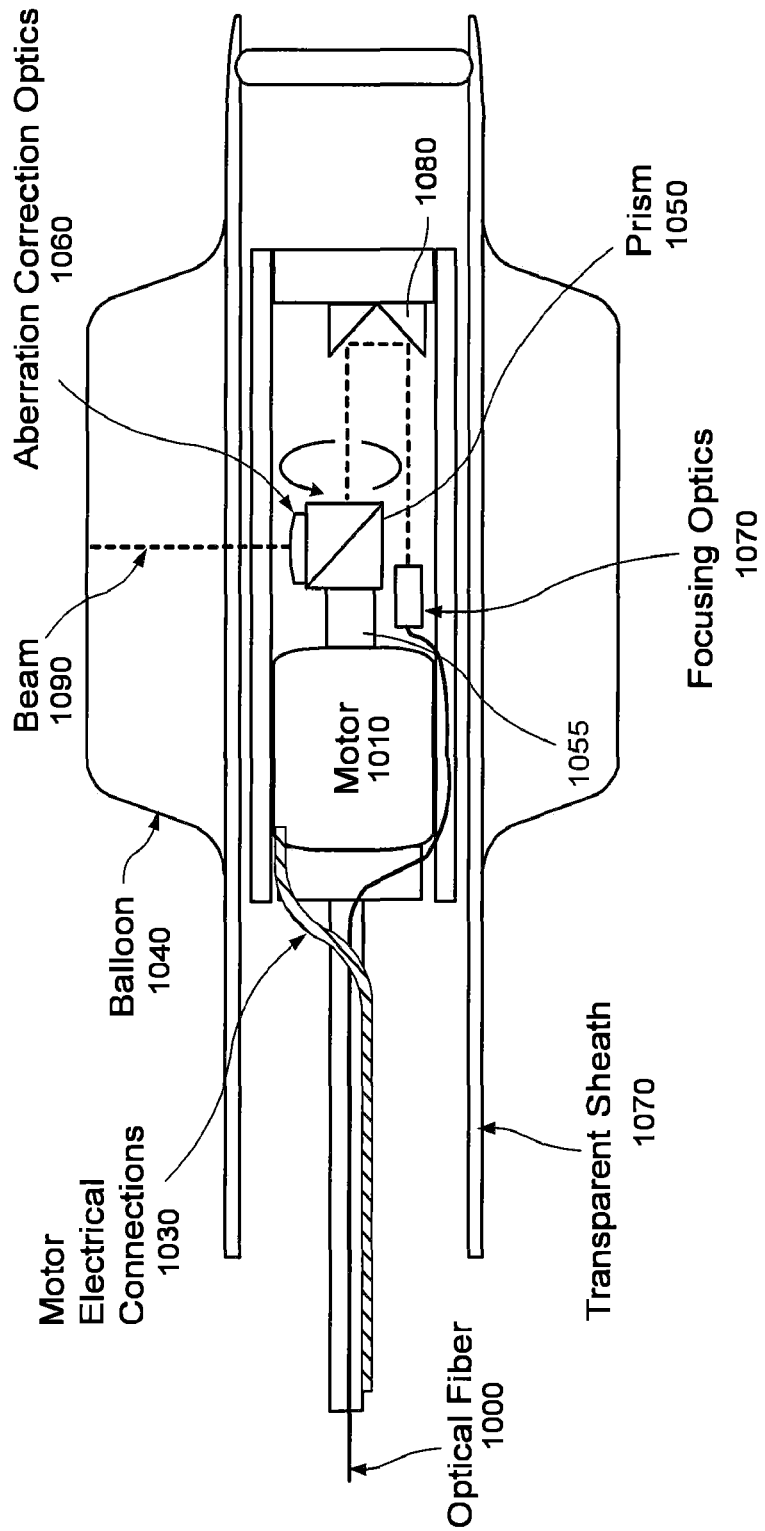
FIG. 14 is a schematic side view of yet another exemplary embodiment of the balloon catheter according to the present invention which uses a forward facing in-catheter motor to rotate the imaging beam.

FIG. 14 shows an exemplary embodiment of a catheter according to the present invention which is similar to that of FIG. 13, but modified by prevent blocking of the imaging beam by motor electrical connections. In this exemplary embodiment, an optical fiber 1000 can be directed past a motor 1010, and reflected by a reflection cap 1080 toward a micro-prism 1050 mounted on a motor shaft 1055. An aberration correcting optic 1060 can be provided on or at the prism 1050. The entire device can be translated to achieve axial scanning.

FIG. 15 shows a side view of yet another exemplary embodiment of a catheter which is similar to that of FIG. 14, but modified to allow for a usage of an additional optical signal which can be used as a motor encoder signal. In this exemplary embodiment, a second optical fiber 1100 directs the light or other electromagnetic radiation past the motor 1100. This light/radiation can be focused and reflected by optics 1110 toward a reflective encoder 1120, which may be located on a motor drive shaft 1111. The reflective encoder 1120 can include alternate areas of high and low reflectivity. As the motor shaft 1111 rotates, the light reflected into this fiber may varies according to information provided by the encoder 1120. By detecting the reflected optical power, the position, velocity, and direction of rotation of the motor 1100 can be measured. This information can be used to control the motor 1100 and/or to register the image with the beam position.

FIG. 16A is a block diagram of an exemplary embodiment of a system (e.g., an OCT system) according to the present invention configured to adjust the reference arm delay in response to the measured balloon position in order to keep the tissue in the system imaging range. This exemplary OCT imaging system can implement auto-ranging. For example, in OCT, OFDI, or SD-OCT systems, the reflectivity can be measured over a limited depth range. If the sample is not located within this depth range, it generally may not be measured. The balloon catheter can center the optical probe in the lumen, and thus maintain the organ luminal surface at approximately a constant depth (balloon radius) from the probe. However, if this is imperfect due to pressure on the balloon distorting its shape, the organ can fall outside the imaging range. In the exemplary embodiment shown in FIG. 16A, the auto-ranging can be used to adjust the imaging depth range to track the position of the liminal organ. This can be effectuated by locating the position 1210 of the surface of the sample (e.g., the balloon surface) by its large reflectivity signal (as shown in FIG. 16B), and adjusting the reference arm delay 1220 to reposition the imaging range accordingly. The reference arm adjustment can involve a modification of the reference arm optical path delay.

Figure 17A:
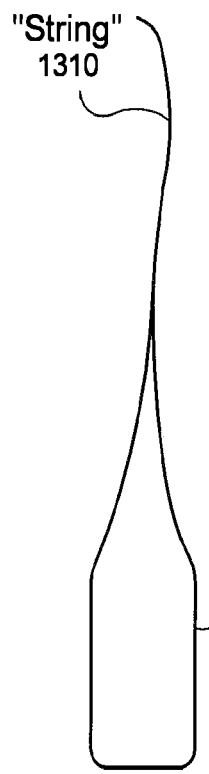
FIG. 17A is a general illustration of an exemplary embodiment of a pill on a string arrangement according to the present invention in which an imaging unit is swallowed by a patient, and connected by a "string" containing optical fiber and/or electrical connections to the imaging unit.
Figure 17B:
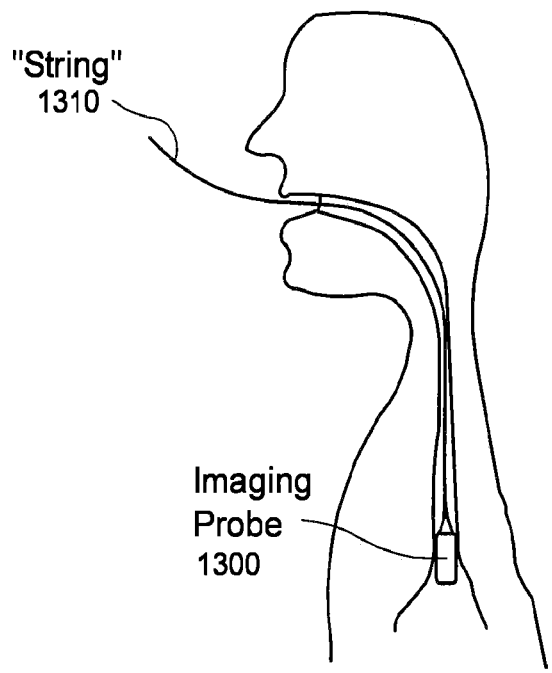
FIG. 17B is an illustration of the arrangement of FIG. 17A in operation while being swallowed by the patient.
Figure 17C:
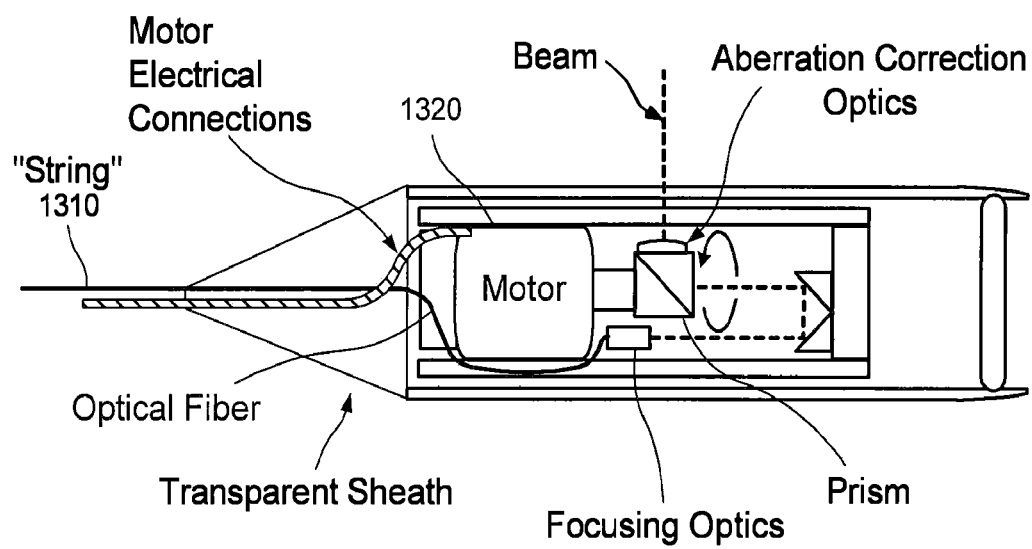
FIG. 17C is a schematic detailed diagram of the arrangement of FIG. 17A.

FIGS. 17A and 17C show illustrations of an exemplary embodiment of a "pill-on-a-string" arrangement according to the present invention in which an imaging unit is swallowed by a patient, and connected by a "string" 1310 containing optical fiber and/or electrical connections to an imaging probe 1300, For example, the imaging probe 1300 (e.g., "pill") containing a micro-motor 1320 is swallowed by the patient (see FIG. 17B). The exemplary micro-motor shown in FIG. 14 can be used as the motor 1320. The probe 1300 can be connected to the system by a "string" 1310 containing fiber optic and electrical connections. By using this "string" 1310, the position of the probe 1300 can be controlled, and the probe 1300 may be placed, for example, in the esophagus of a patient. After imaging, the probe 1300 can be retrieved using this "string"1310.

Figure 18A:
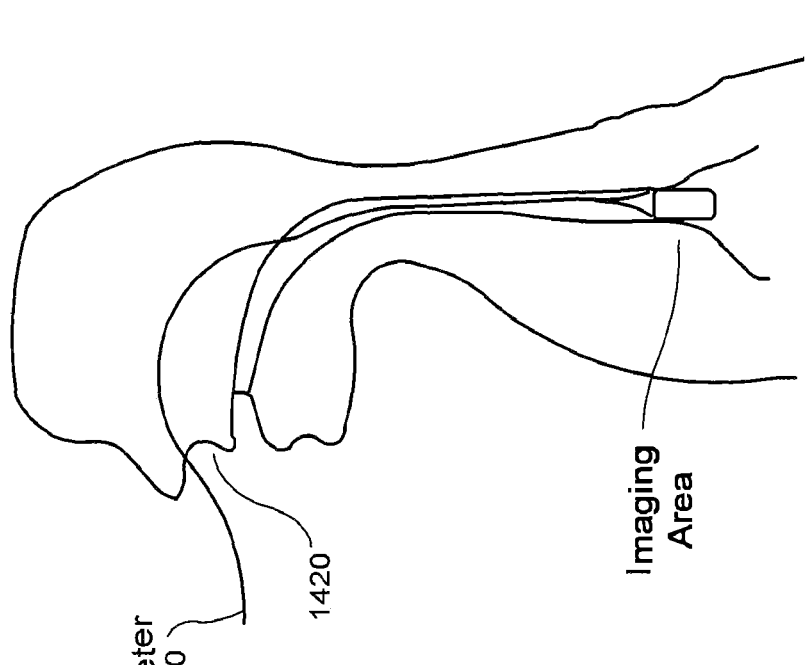
FIG. 18A is an illustration of a trans-oral placement of an exemplary embodiment of the catheter according to the present invention.
Figure 18B:
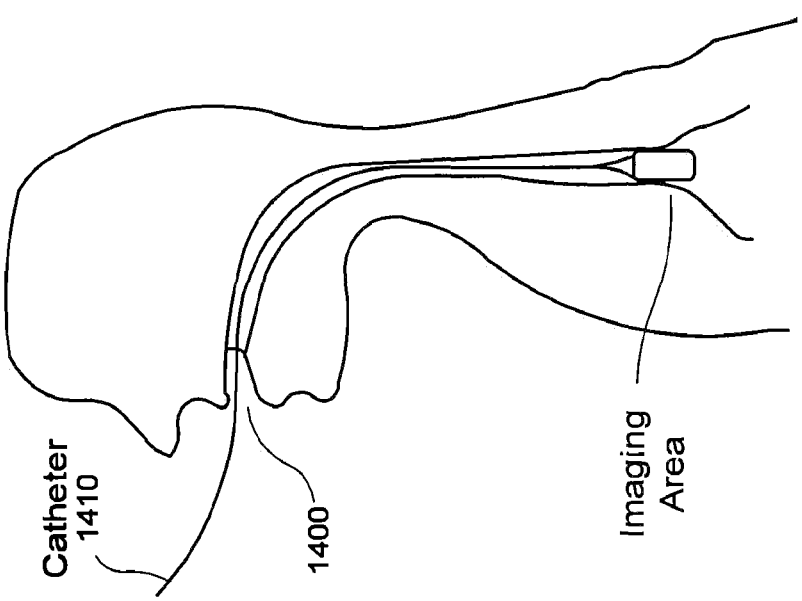
FIG. 18B is an illustration of a trans-nasal placement of an exemplary embodiment of a trans-oral catheter according to the present invention.

FIGS. 18A and 18B show illustration of trans-oral placement and trans-nasal placement, respectively, of an exemplary embodiment of the catheter according to the present invention, e.g., for the upper gastro-intestinal tract imaging. In FIG. 18B, the catheter 1410 can be placed through the mouth 1400, i.e. trans-orally. In FIG. 18B, the catheter 1410 may be placed through the nasal orifice 1420, i.e. trans-nasally. Trans-nasal designs can have the advantage of not requiring patient sedation, but should be small in diameter. A relatively small size of the fiber optical imaging core according to the exemplary embodiment of the present invention can allow for its implementation trans-nasally.

FIGS. 19A and 19B show schematic diagrams of an exemplary embodiment of a wire cage centering arrangement of an exemplary catheter according to the present invention in a closed mode, and during the opening starting from a distal portion thereof, respectively. For example, the catheter may use wire strands instead of a balloon to expand and center the inner optical core in the luminal organ. The catheter can include an outer sheath 1510, a set of expandable wire stents 1500 and an inner core 1530. After the placement of the catheter, the other sheath may be retracted to allow the wire stenting 1500 to expand the organ. After imaging, the outer sheath 1510 may be extended to collapses the wire stenting, and the catheter can be removed.

Figure 20:
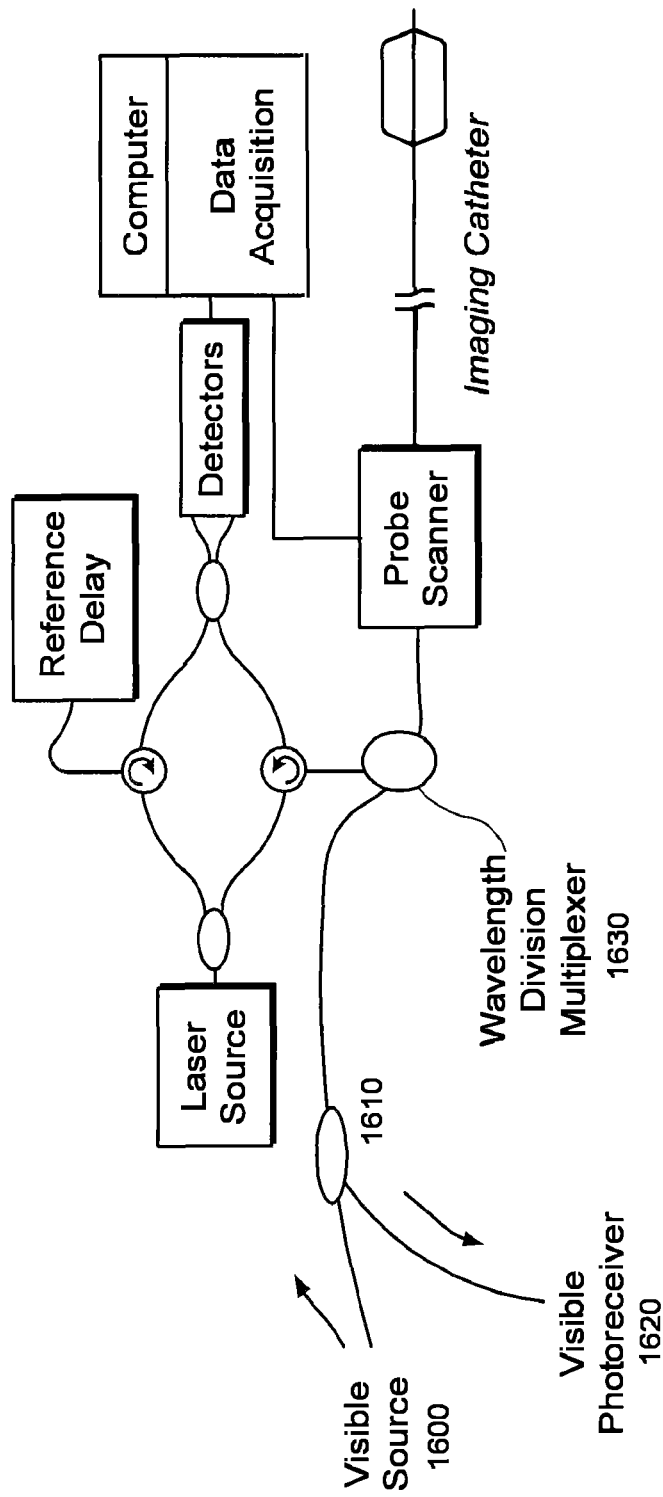
FIG. 20 is a block diagram of an optical coherence tomography screening device combined with a further optical imaging arrangement operating at a second wavelength band according to an exemplary embodiment of the present invention.

FIG. 20 illustrates a block diagram of an exemplary embodiment of an imaging system according to the present invention in which a second wavelength band can be multiplexed into the catheter to achieve a second imaging modality. This modality could, for example, be visible light reflectance imaging or fluorescence imaging. In this exemplary arrangement, a visible light source 1600 can be coupled to the imaging catheter (e.g., as the one shown in FIG. 3) via a wavelength division multiplexer 1630 which combined the second wavelength band with a primary imaging wavelength band, e.g., typically infrared. The visible light reflected from the sample can be separated from a primary imaging wavelength band by this wavelength division multiplexer 1630, and directed toward a photoreceiver 1620 by a splitter 1610.

Figure 21:
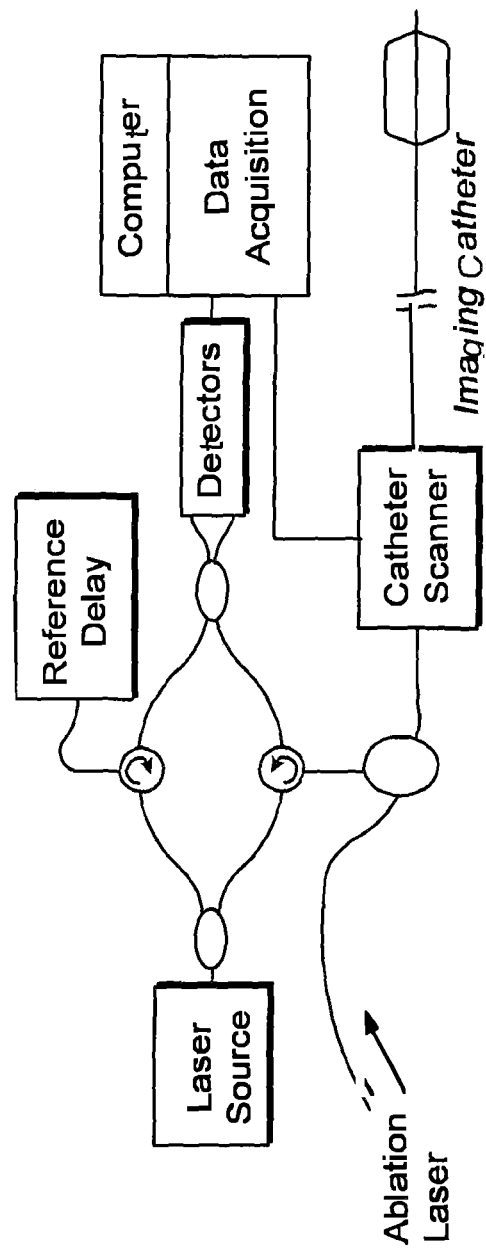
FIG. 21 is a block diagram an optical coherence tomography imaging system configured to allow a combination of an ablation beam with the imaging beam in a sample arm in accordance with another exemplary embodiment of the present invention.

An advantageous additional functionality for an epithelial luminal organ imaging system can be a capability to direct subsequent inspection to a region of interest identified in the imaging dataset. For example, if an area of dysplasia is detected in a region of the esophagus, one might want to direct an endoscope to take a tissue biopsy in that area to confirm that diagnosis. A method and system can be used for placing a visible mark on the tissue at a location of interest identified in the image dataset. FIG. 21 shows a block diagram of still another exemplary embodiment of the arrangement according to the present invention for achieving this by the coupling of an ablation laser 1700 through a fiber optic wavelength division multiplexer 1710 to the imaging catheter. The ablation laser 1700 can be configured to include an optical power and wavelength sufficient to create superficial lesions on the luminal organ. These lesions can be seen endoscopically, and may be used as markers for further investigation, e.g., biopsy. As shown in FIG. 21, the catheter can point to an area to be marked and made stationary. The ablation laser is then turned on for a duration sufficient to create the visible lesion.

Figure 22:
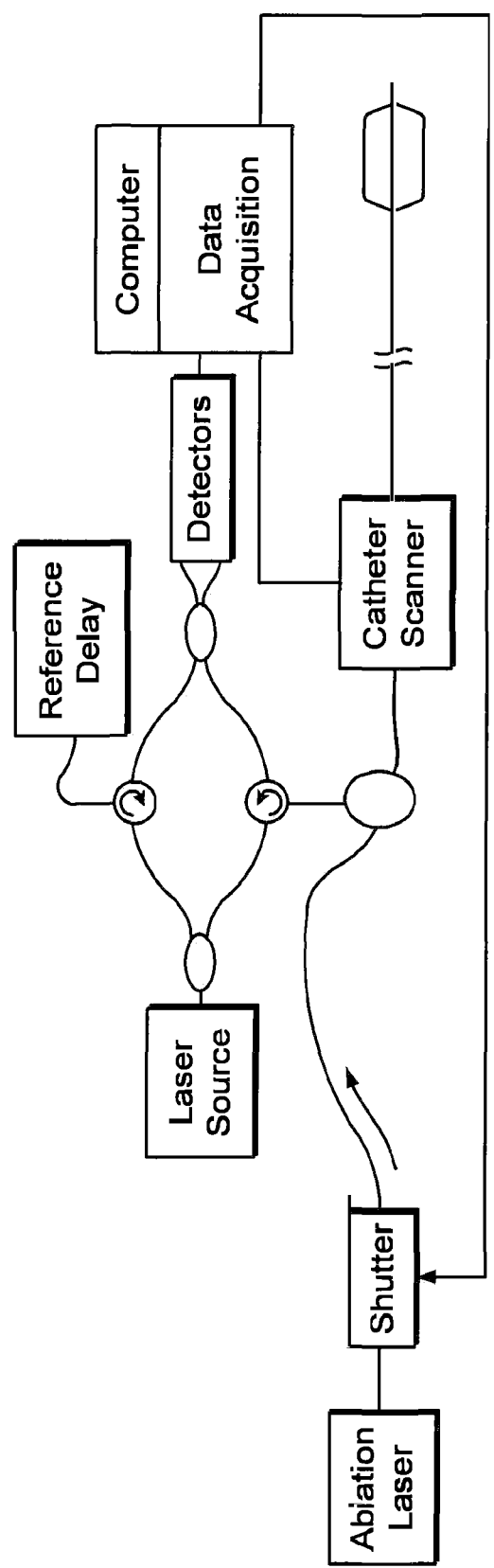
FIG. 22 is a block diagram an optical coherence tomography imaging system configured to allow an on-the-fly ablation in accordance with yet another exemplary embodiment of the present invention.

FIG. 22 shows an alternate exemplary embodiment of the arrangement according to the present invention in which the catheter scanner is not stopped but instead ablation is performed on-the-fly. The data acquisition unit 1720 is programmed to open an optical shutter 1730 when the catheter is pointed at the region of interest. The optical shutter 1730 can transmit the ablation light when open, and blocks in when closed. For example, the catheter can remain in motion.

Figures 23A, 23B:
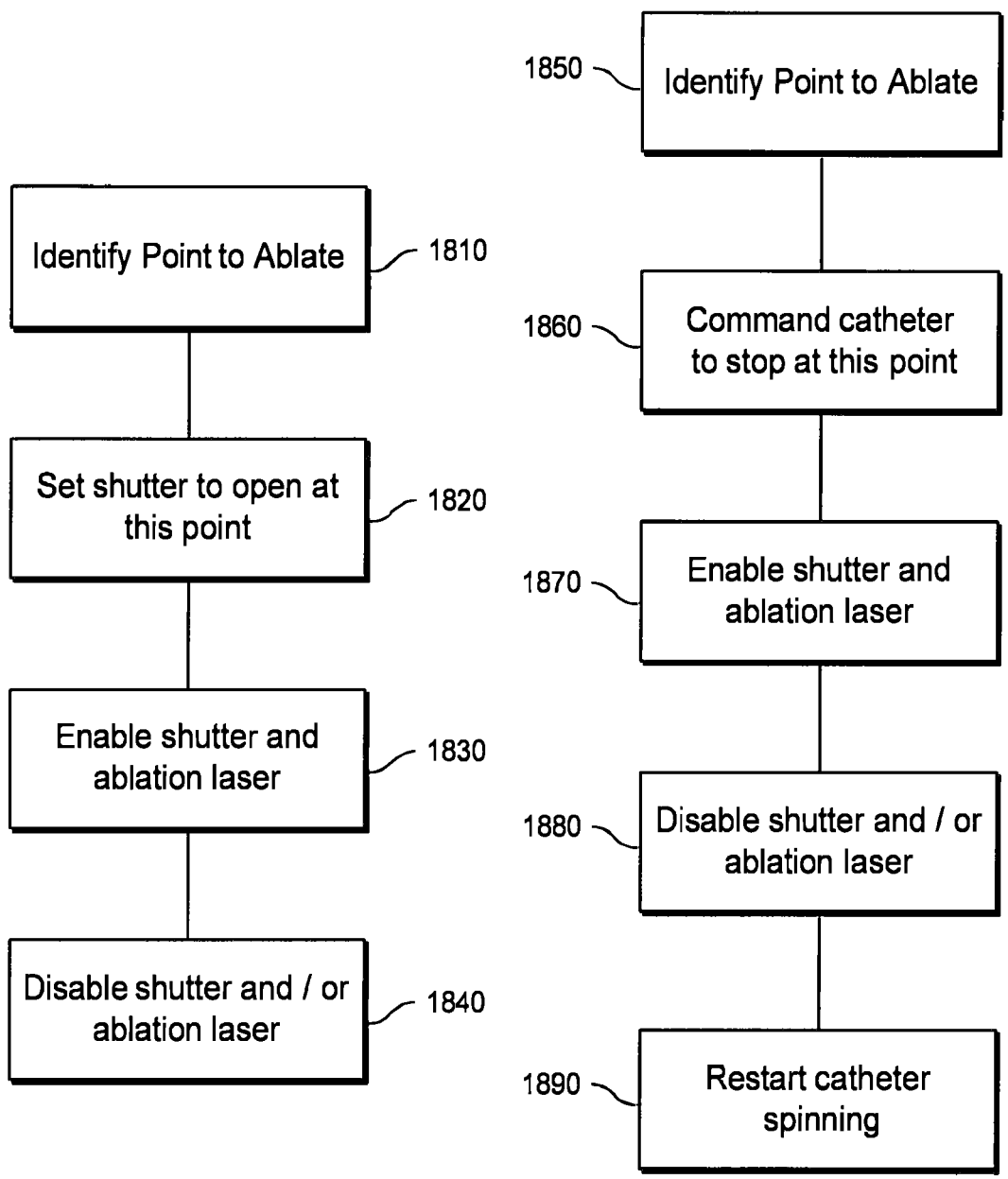
FIG. 23A is a flow diagram of an exemplary embodiment of a process for ablation marking according to the present invention for the on-the-fly ablation.
FIG. 23B is a flow diagram of an exemplary embodiment of a process for ablation marking according to the present invention for stopping and ablating.

FIG. 23A shows a flow diagram of an exemplary embodiment of a process for ablation marking according to the present invention for the on-the-fly ablation in the area of interest. In particular, a point to oblate is identified in step 1810. In step 1820, the shutter is set to open at such point. In step 1830, the shutter and ablation laser is enabled, and then, in step 1840, the shutter and/or the ablation laser is disabled.

FIG. 23B shows a flow diagram of an exemplary embodiment of a process for ablation marking according to the present invention for stopping and ablating in the are of interest. In particular, a point to oblate is identified in step 1850. In step 1860, catheter is commanded to stop at that point. In step 1870, the shutter and ablation laser is enabled, and then, in step 1880, the shutter and/or the ablation laser is disabled. The spinning of the catheter is restarted in step 1890.

Figure 24:
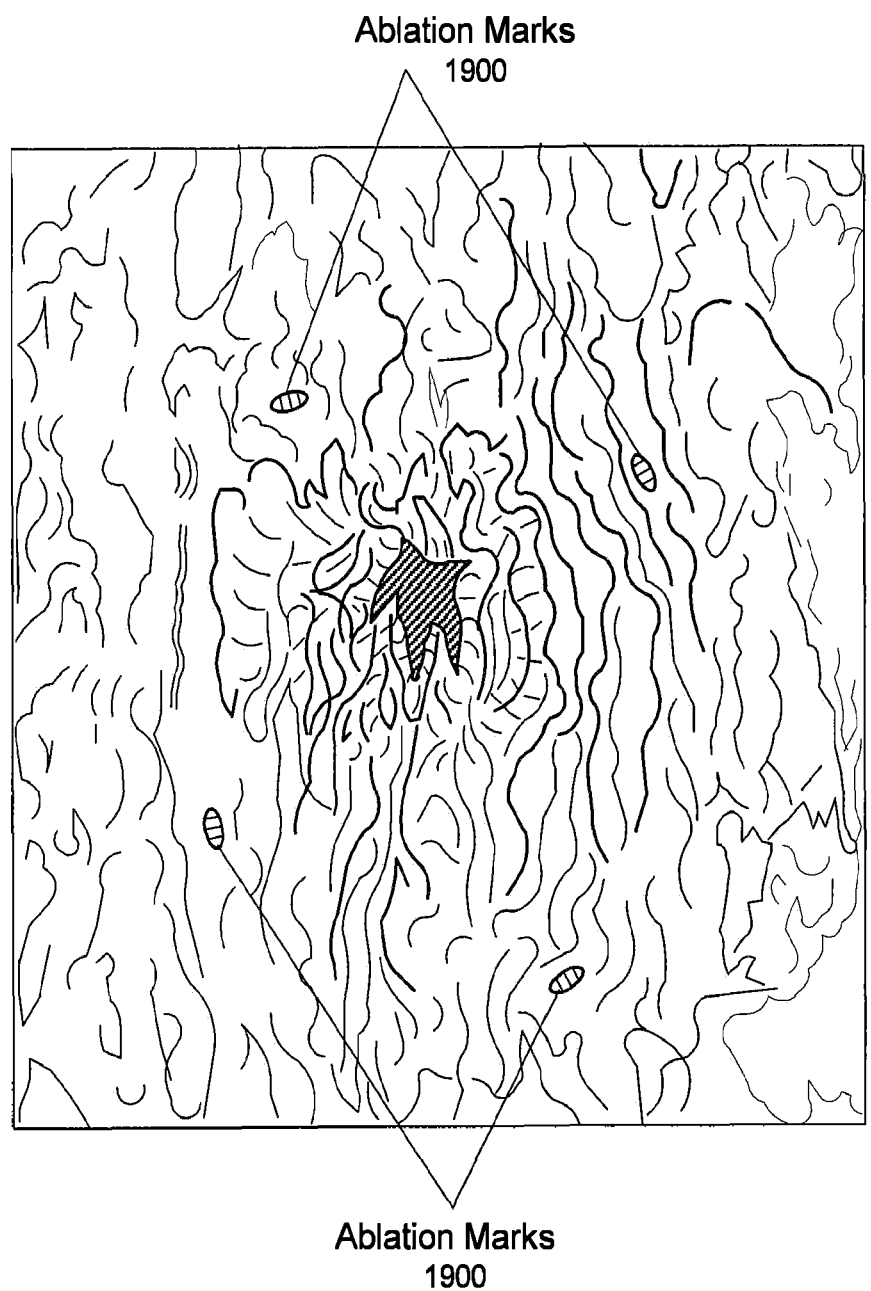
FIG. 24 is an endoscopic image showing the visibility of ablation marks in a swine esophagus for imaging by the exemplary embodiments of the arrangements and processes according to the present invention.

FIG. 24 shows an exemplary image (generated using the exemplary embodiments of the present invention) which includes ablation marking regions of interest. For example, the ablation marks 1900 are shown which are created in the esophagus using a series of lasers of wavelengths 1440 nm to 1480 nm and an optical power of approximately 300 mW for a duration of approximately 1 second.

Figure 25A:
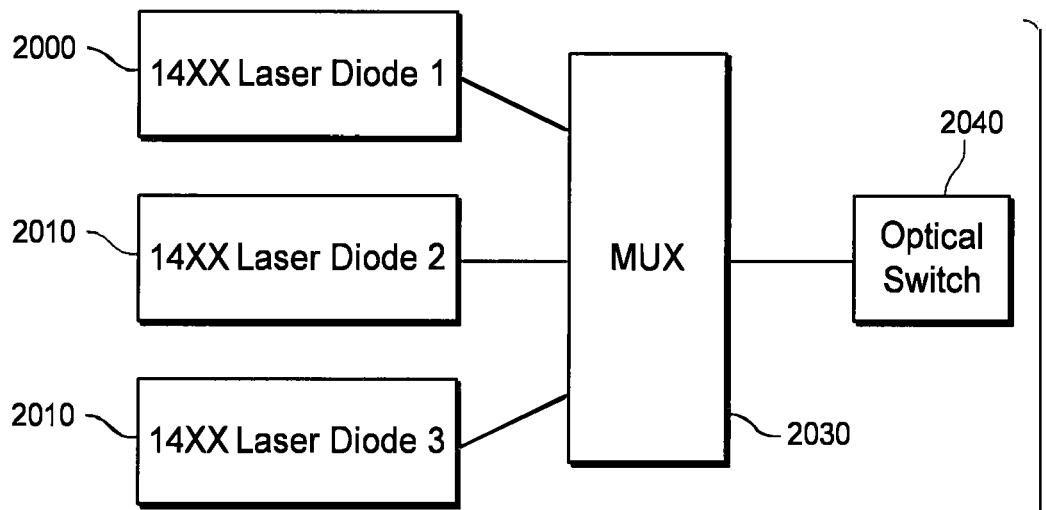
FIG. 25A is a block diagram of an exemplary embodiment of the arrangement according to the present invention including an ablation laser source which uses multiple lasers of wavelengths in the 1400-1499 nm range that are multiplexed together with an optical switch as a shutter, with the optical switch after the multiplexer (MUX)
Figure 25B:
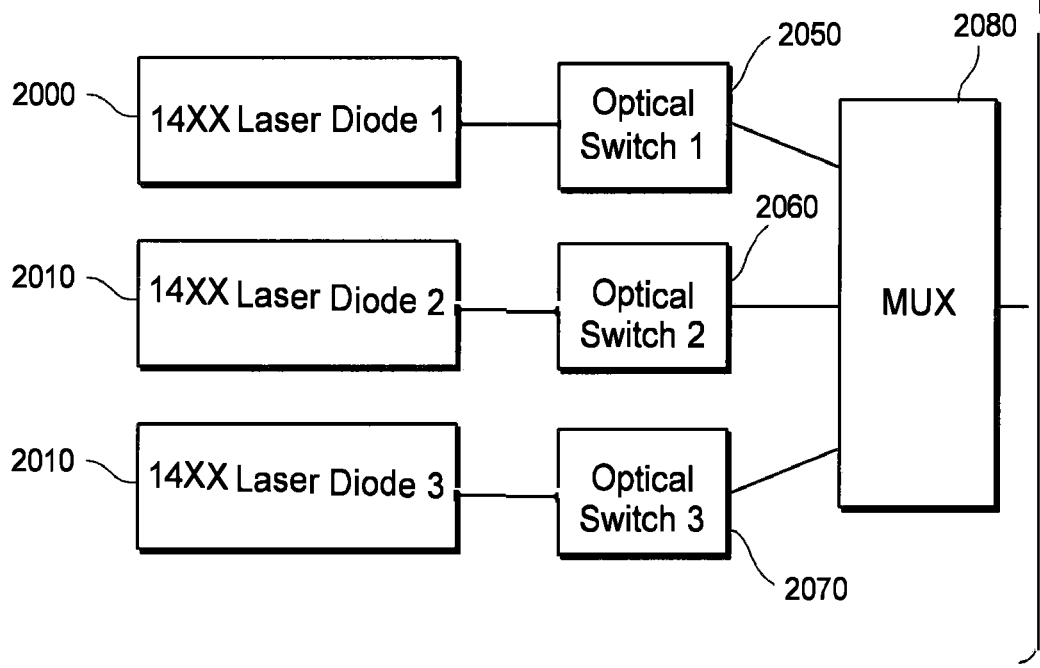
FIG. 25B is a block diagram of the exemplary embodiment of the arrangement according to the present invention including an ablation laser source which uses multiple lasers of wavelengths in the 1400-1499 nm range that are multiplexed together with an optical switch as a shutter, with separate optical switches for each laser located before the multiplexer (MUX)

FIGS. 25A and 25B show flow and block diagrams of interconnections of an exemplary embodiments of the arrangement according to the present invention, and implementations of an exemplary method of the present invention which can combining multiple ablation lasers and an optical switch (shutter) of the exemplary arrangement. In FIG. 25A, multiple lasers 2000, 2010, and 2020 can be combined using a multiplexer (MUX) 2030, which can be a wavelength-division multiplexer, a polarization-multiplexer, and/or a combination of both, followed by a single shutter 2040. In FIG. 25B, each laser 2000, 2010, 2020 can use a separate shutter 2050, 2060, 2070, which may be subsequently combined using a MUX 2080.

Figure 26:
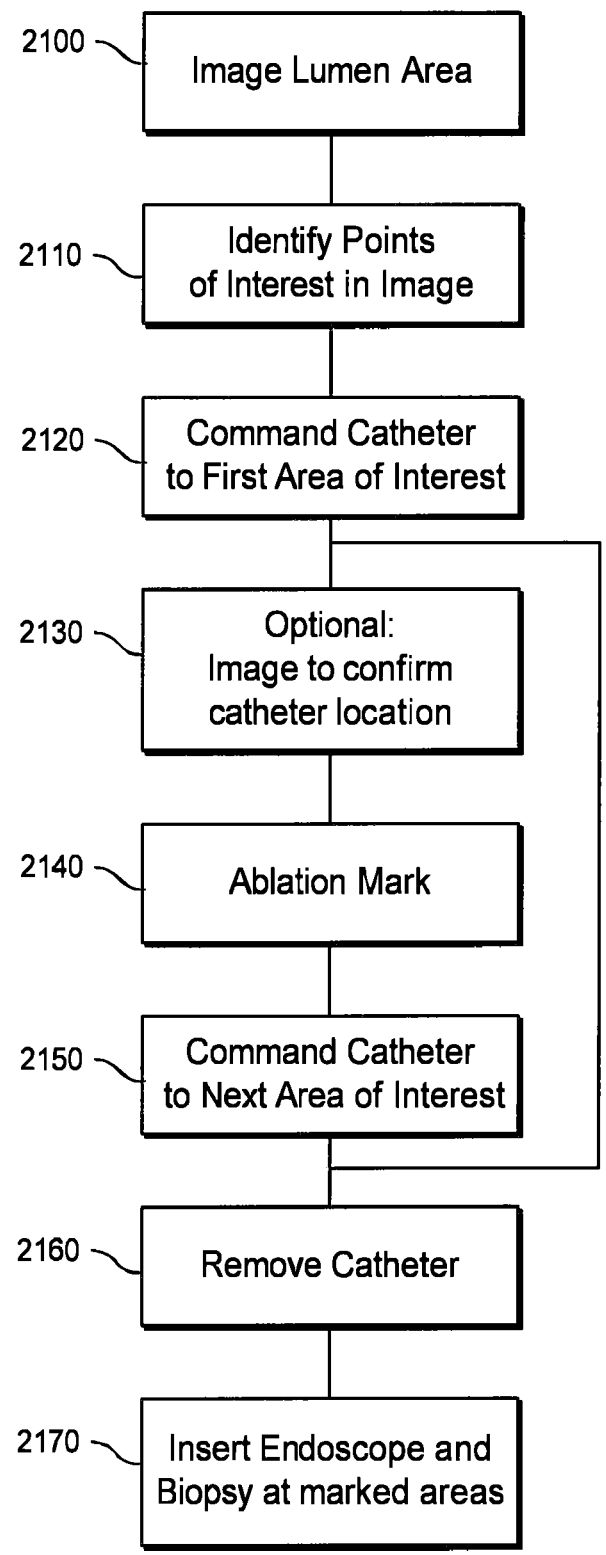
FIG. 26 is a flow diagram of an exemplary process performed by an imaging system according to the present invention which marks areas of interest identified in a completed imaging session.

FIG. 26 shows a block diagram of an exemplary embodiment of a method for examining a luminal organ and subsequent marking of areas of interest. In step 2100, the lumen area is imaged in full. Then, in step 2110, areas of interest are identified using either automated algorithms or inspection by an operator. In step 2120, the catheter is directed to the area of the first region of interest. Imaging is optionally commenced and the catheter position is adjusted interactively to re-find the region of interest in step 2130. This re-finding procedure can compensate for displacement of the catheter due to, for example, peristaltic motion in the esophagus. Next, in step 2140, a single or series of ablation marks can be made adjacent to or around the region of interest. This procedure is repeated for each of the areas of interest (steps 2150, 2130, 2140, and so on). In step 2160, the catheter is then removed and additionally inspection or biopsy is performed as those marked areas in step 2170.

Figure 27:
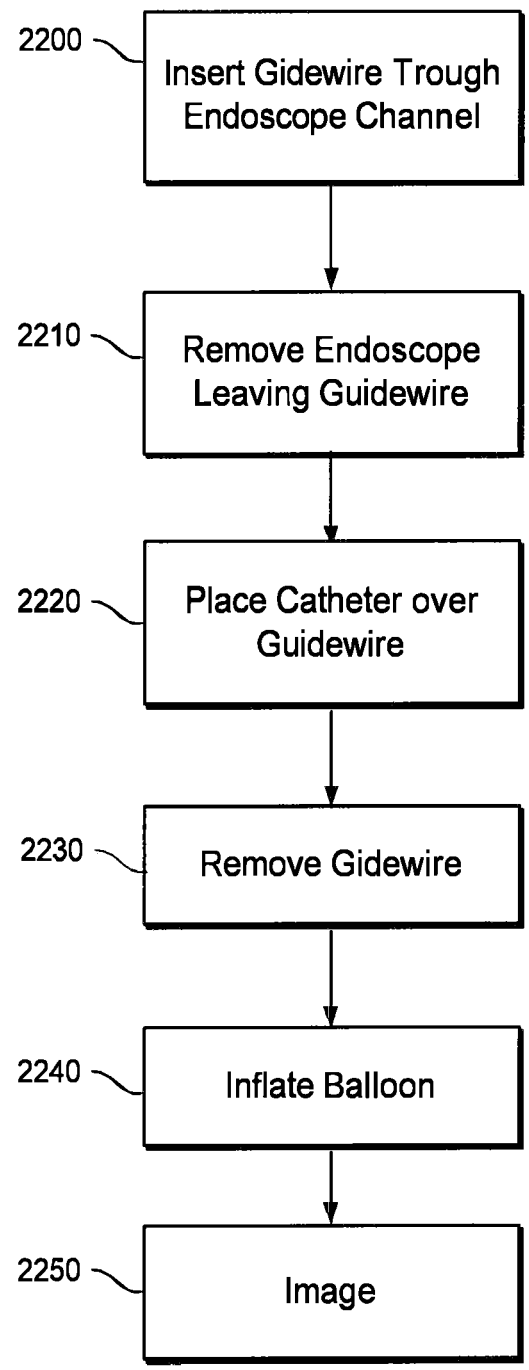
FIG. 27 is a flow diagram of an exemplary procedure for placement of exemplary embodiments of the over-the-wire catheter or the rapid-exchange catheter according to the present invention.

FIG. 27 shows an exemplary embodiment of a procedure according to the present invention for placement of the imaging catheter using endoscopic placement of the guidewire. In particular, the guidewire is inserted through an endoscope channel in step 2200. In step 2210, the endoscope is then removed, leaving the guidewire. In step 2220, the catheter is placed over the guidewire as described above with reference to various exemplary embodiments of the present invention. In step 2230, the guidewire is then removed. Further, in step 2240, the balloon is inflated, and imaging begins in step 2250.

Figure 28A:
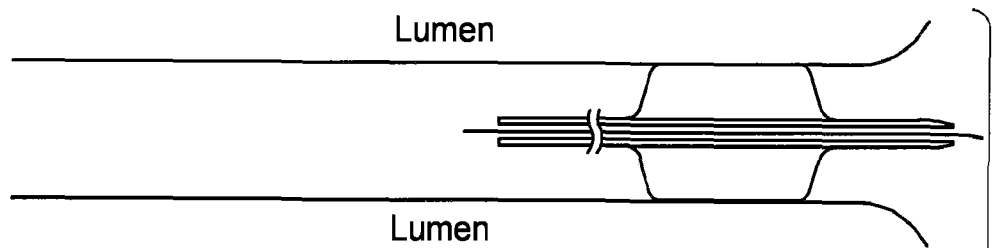
FIGS. 28A-C are illustrations of multiple probe placements to image over an area larger than the area of the imaging window of the probe in various stages in accordance with an exemplary embodiment of the present invention.
Figure 28B:
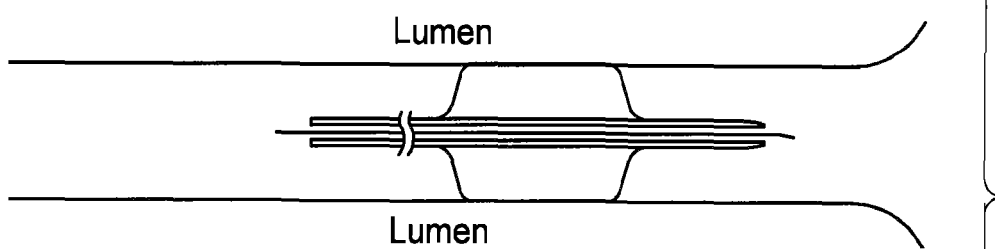
Figure 28C:
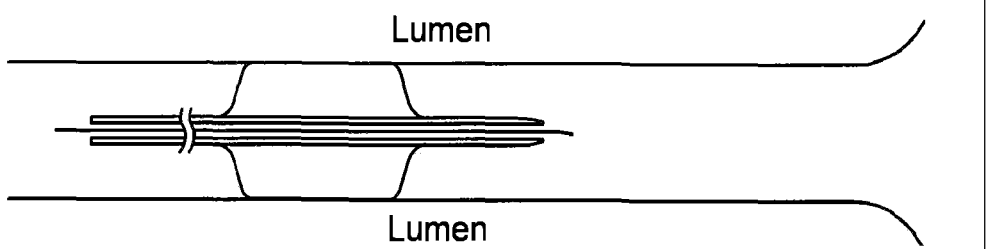

FIGS. 28A-28C show exemplary steps of an operation which utilizes the exemplary arrangement of the present invention for imaging over an area larger than the balloon length by multiple placements of the balloon. The imaging sets obtained with the balloon in positions shown in FIGS. 28A-28C can be combined to yield imaging over a large area.

Figure 29:
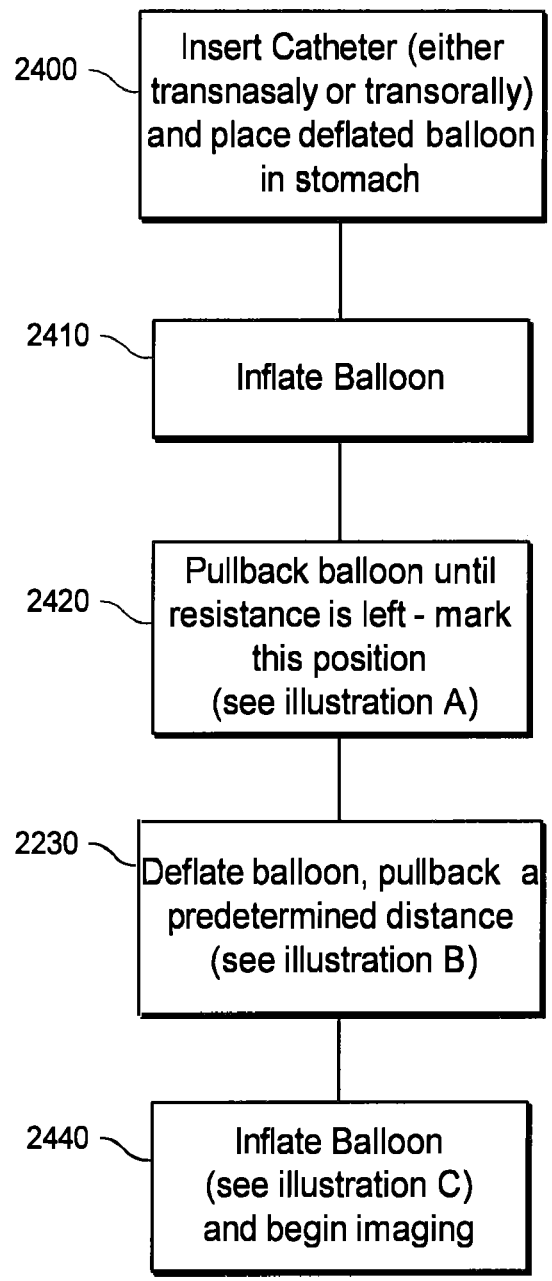
FIG. 29 is a flow diagram of an exemplary placement procedure according to the present invention in which the balloon is inflated in the stomach and pulled back until resistance is encountered, thereby locating the proximal end of the balloon with a Gastroesophageal junction.
Figure 30A:
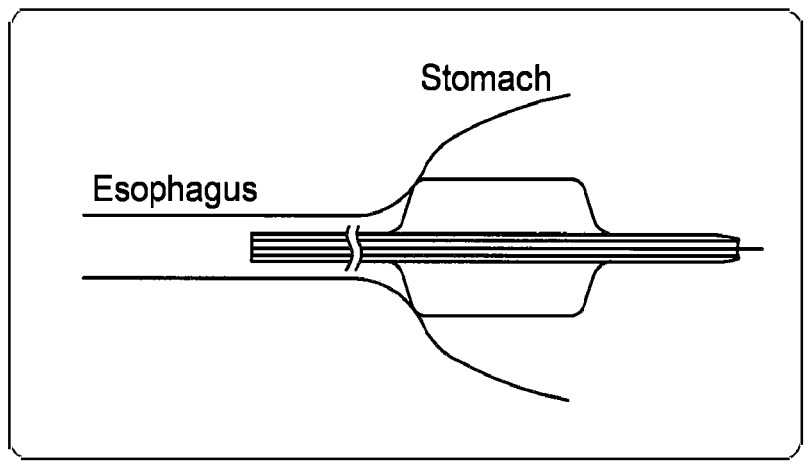
FIGS. 30A-30C are the exemplary steps performed by the exemplary arrangement using the exemplary method of FIG. 29.
Figure 30B:
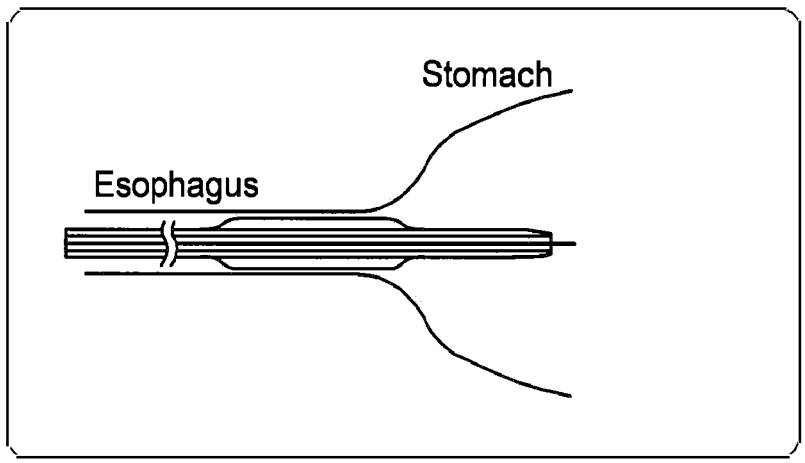
Figure 30C:
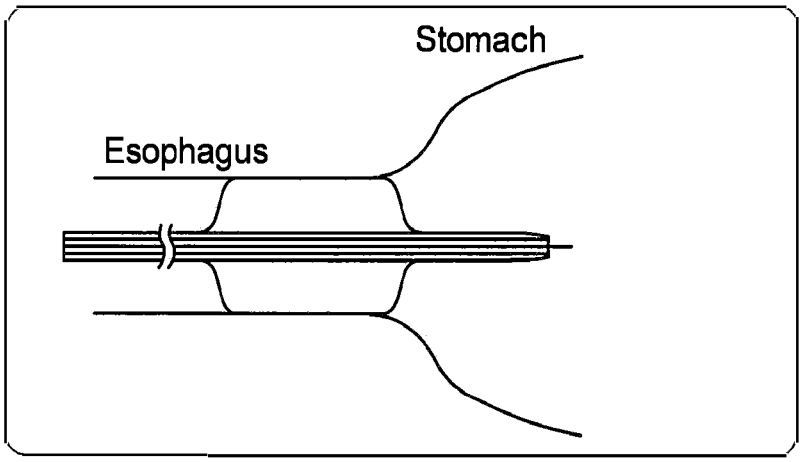

FIG. 29 shows an exemplary embodiment of a method for placement of an imaging probe at the junction between the tubular esophagus and the stomach. FIGS. 30A-30C show the exemplary steps performed by the exemplary arrangement of the present invention using the method of FIG. 29. In step 2400, the catheter is inserted with the balloon deflated and placed in the stomach. In step 2410, the balloon is inflated (FIG. 30A), and in step 2420, pulled back until resistance is felt, thereby locating the proximal side of the balloon at the gastro-esophageal junction (junction between the stomach and esophagus). Next, in step 2430, the balloon is partially deflated (FIG. 30B), and the catheter is pulled back a predefined amount such as the balloon length. Further, in step 2440, the balloon is inflated, and imaging proceeds with the catheter located at the gastro-esophageal junction (FIG. 30C).

In an additional exemplary embodiment of the present invention, the imaging system can be operated in an abbreviated imaging mode (e.g., scout imaging) to determine if the catheter is properly located in the organ. A full comprehensive imaging can begin after proper catheter placement is confirmed. In yet another exemplary embodiment of the present invention, the balloon centering catheter can be inflated with materials that are optically transparent other than air such as but not limited to water, heavy water ($D_2O$), or oil. In still another exemplary embodiment of the present invention, the laser marking may utilize previously applied exogenous agents in the organ to provide absorption of the marking laser. In a further exemplary embodiment of the present invention, a lubricating agent can be used to aid insertion of the catheter. In another exemplary embodiment of the present invention, a mucosal removal agent can be used prior to imaging to reduce mucous in the organ which can reduce imaging quality.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with and/or implement any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus for obtaining data from a luminal sample, comprising:
   a scanning optical arrangement configured to transmit at least one electromagnetic radiation to and from the luminal sample;
   a pill-shaped housing containing the scanning optical arrangement; and
   a tether comprising a waveguide attached to the pill-shaped housing,
   the waveguide configured to transmit the at least one electromagnetic radiation to and from the scanning optical arrangement.

2. The apparatus of claim 1, wherein the scanning optical arrangement comprises a scanning confocal microscopy system.

3. The apparatus of claim 2, wherein the scanning confocal microscopy system comprises a spectrally encoded confocal microscopy system.

4. The apparatus of claim 3, wherein the scanning optical arrangement comprises a rotating optical component that transmits the at least one electromagnetic radiation to and from the luminal sample.

5. The apparatus of claim 4, wherein the scanning optical arrangement comprises an ablation laser optically coupled to the waveguide.

6. The apparatus of claim 5, further comprising an imaging source to provide the at least one electromagnetic radiation.

7. The apparatus of claim 6, wherein the scanning optical arrangement further comprises a processor configured to communicate with the ablation laser, the rotating optical component, and the imaging source, the processor being configured to:

receive, using the waveguide, data associated with a portion of the luminal sample, and cause, based on the data, the ablation laser to create a visible change at the portion of the luminal sample using laser radiation transmitted using the waveguide.

8. The apparatus of claim 7, wherein the visible change comprises a superficial lesion.

9. The apparatus of claim 8, wherein the data comprises image data.

10. The apparatus of claim 9, wherein the processor is further configured to, using further image data based on the visible change at the portion of the luminal sample, automatically effectuate at least one of a removal or a destruction of at least one section of the portion of the luminal sample.

11. The apparatus of claim 10, wherein the further image data comprises visible image data.

12. The apparatus of claim 10, wherein the processor is further configured to obtain the further image data after the visible change is effectuated.

13. The apparatus of claim 10, wherein the at least one image comprises a volumetric image of the portion of the luminal sample.

14. The apparatus of claim 13, wherein the volumetric image comprises a cylindrical image.

* * * * *

UNITED STATES PATENT AND TRADEMARK OFFICE
CERTIFICATE OF CORRECTION

| | |
|---|---|
| PATENT NO. | : 11,660,001 B2 |
| APPLICATION NO. | : 17/130585 |
| DATED | : May 30, 2023 |
| INVENTOR(S) | : Guillermo J. Tearney et al. |

It is certified that error appears in the above-identified patent and that said Letters Patent is hereby corrected as shown below:

In the Specification

Column 11, Line 14, "liminal" should be --luminal--.

Signed and Sealed this
Fifteenth Day of August, 2023

Katherine Kelly Vidal
*Director of the United States Patent and Trademark Office*